(12) United States Patent
Voit et al.

(10) Patent No.: US 10,786,671 B2
(45) Date of Patent: Sep. 29, 2020

(54) SPINAL CORD STIMULATOR DEVICE AND METHODS OF MANUFACTURE AND USE THEREOF

(71) Applicants: Board of Regents, The University of Texas System, Austin, TX (US); Cornell University, Ithaca, NY (US)

(72) Inventors: Walter E. Voit, Austin, TX (US); Aldo Garcia-Sandoval, Austin, TX (US); Jason Carmel, White Plains, NY (US)

(73) Assignees: Board of Regents, The University of Texas System, Austin, TX (US); Cornell University, Ithaca, NY (US)

( * ) Notice: Subject to any disclaimer, the term of this patent is extended or adjusted under 35 U.S.C. 154(b) by 0 days.

(21) Appl. No.: 16/344,100

(22) PCT Filed: Oct. 27, 2017

(86) PCT No.: PCT/US2017/058857
§ 371 (c)(1),
(2) Date: Apr. 23, 2019

(87) PCT Pub. No.: WO2018/089215
PCT Pub. Date: May 17, 2018

(65) Prior Publication Data
US 2019/0336771 A1 Nov. 7, 2019

Related U.S. Application Data

(60) Provisional application No. 62/420,814, filed on Nov. 11, 2016.

(51) Int. Cl.
*A61N 1/36* (2006.01)
*A61N 1/05* (2006.01)

(52) U.S. Cl.
CPC ....... *A61N 1/36062* (2017.08); *A61N 1/0553* (2013.01); *A61N 1/36125* (2013.01)

(58) Field of Classification Search
CPC ............ A61N 1/36062; A61N 1/36125; A61N 1/0553
See application file for complete search history.

(56) References Cited

U.S. PATENT DOCUMENTS

| 6,024,702 A | 2/2000 | Iversen |
|---|---|---|
| 6,594,515 B2 | 7/2003 | Watson |

(Continued)

FOREIGN PATENT DOCUMENTS

| WO | 199510227 A1 | 4/1995 |
|---|---|---|
| WO | 2005002665 A2 | 1/2005 |
| WO | 2018089215 A1 | 5/2018 |

OTHER PUBLICATIONS

Sherman, et al.; "Measurements of the Normal Cervical Spinal Cord on MR Imaging"; American Society of Neuroradiology; May 5, 1989; pp. 369-372.

(Continued)

*Primary Examiner* — Catherine M Voorhees

(57) ABSTRACT

A spinal cord stimulator device, including an implantation paddle, a connection segment and an encapsulant. The implantation paddle includes at least one pair of electrode stimulation pads, each of the electrode stimulation pads connected to ends of separate thin film electrode leads, wherein the electrode stimulation pads and the thin film electrode leads are sandwiched between softening polymer layers. The connection segment includes insulated wire leads, one end of each of the wire leads can be connected to contact pads on opposite ends of each one of the thin film leads at separated coupling joints. The encapsulant encompasses portions of the implantation paddle, including encompassing portions of the softening polymer layers surrounding the contact pads, the coupling joints and portions of the connection segment including portions of the wire leads next to the coupling joints. Methods of manufacturing device and using the device for spinal cord stimulation are also described.

19 Claims, 16 Drawing Sheets

(56) References Cited

U.S. PATENT DOCUMENTS

| | | | |
|---|---|---|---|
| 6,624,510 B1 | 9/2003 | Chan et al. | |
| 2003/0011967 A1 | 1/2003 | Nielsen et al. | |
| 2006/0106440 A1* | 5/2006 | Chandran | A61N 1/0551 607/117 |
| 2010/0280561 A1* | 11/2010 | Song | C08G 63/08 606/86 R |
| 2011/0230747 A1* | 9/2011 | Rogers | A61B 5/05 600/377 |
| 2011/0307042 A1 | 12/2011 | Decarmine | |
| 2012/0035615 A1 | 2/2012 | Koester et al. | |
| 2014/0262462 A1* | 9/2014 | Shah | H05K 3/4007 174/257 |

OTHER PUBLICATIONS

DeVos, et al.; "Spinal Cord Stimulation With Hybrid Lead Relieves Pain in Lower Back and Legs"; Neuromodulation: Technology at the Neural Interface: onlinelibrary.wiley.com; DOI:10,1111/j.1525-1403.2011.00404.x; 2011 International Neuromodulation Society; www.neuromodulationjournal.com; Dec. 27, 2010; pp. 118-123.

Kumar, et al.; "The Effects of Spinal Cord Stimulation in Neuropathic Pain Are Sustained: A 24-month Follow-up of the Prospective Randomized Controlled Multicenter Trial of the Effectiveness of Spinal Cord Stimulation"; Clinical Trial; Neurosurgery; www.neurosurgery.online.com; vol. 63, No. 4, Oct. 2008, pp. 762-770.

Oakley, et al.; "A New Spinal Cord Stimulation Effectively Relieves Chronic, Intractable Pain: A Multicenter Prospective Clinical Study" ; Original Article; Neuromodulation: Technology at the Neural Interface; http://www.plackwell-synergy.com./loi/ner; vol. 10, No. 3, 2007; 17 pgs.

Kumar, et al.; "Spinal cord stimulation versus conventional medical management for neuropathic pain: A multicentre randomised controlled trail in patients with failed back surgery syndrome"; Pain; International Association for the Study of Pain; www.elsevier.com/locate/pain; 2007; 10 pgs.

Ohnmeiss, et al.; "Prospective Outcome Evalution of Spinal Cord Stiumulation in Patients with Intractable Leg Pain", Spine, vol. 21, No. 11; Lippincott-Raven Publishers; 1996; pp. 1344-1350.

"Microposit MF-319 Developer"; Shipley; MD MF-319B 0391; 1997; 4 pgs.

\* cited by examiner

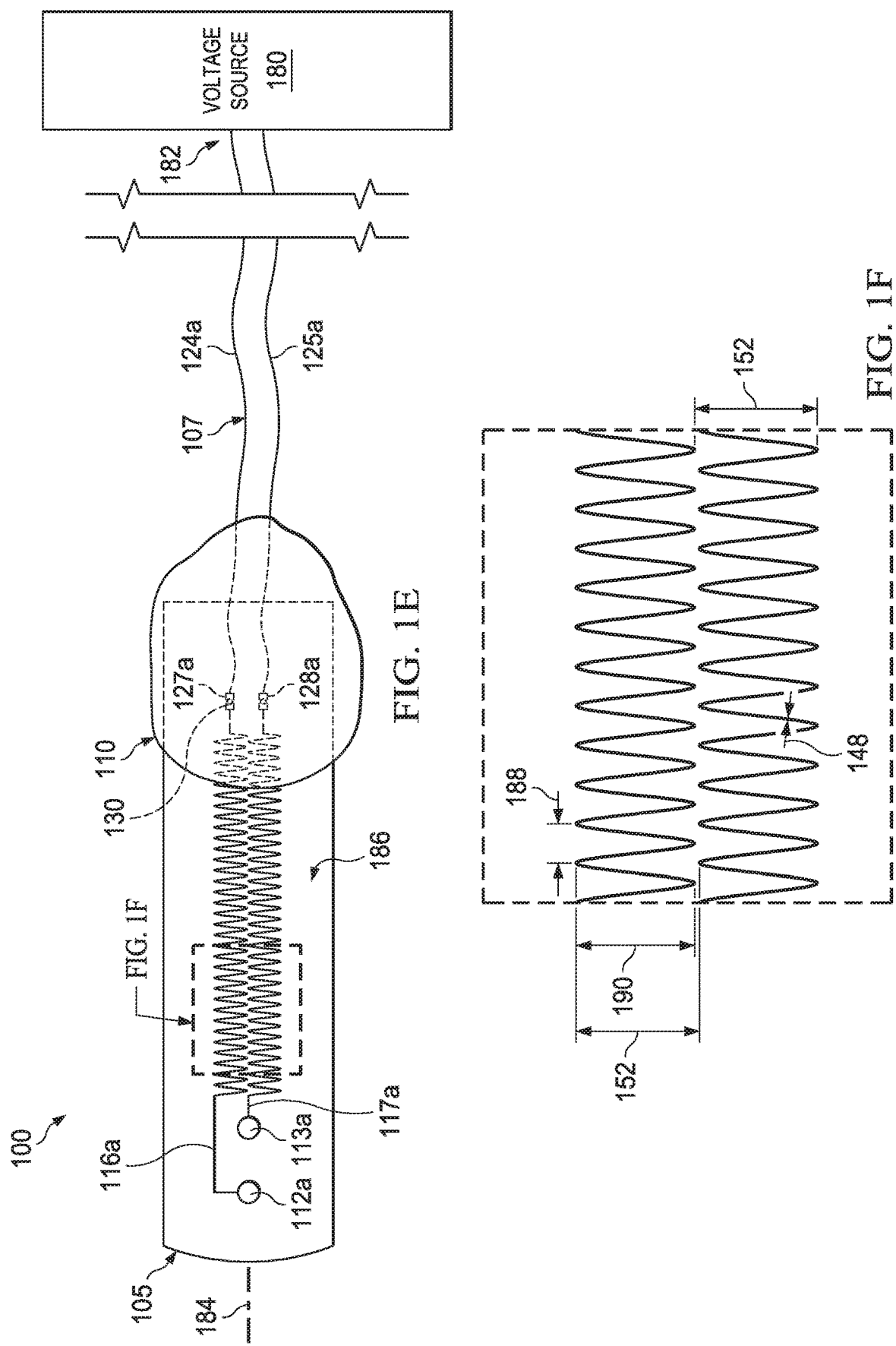

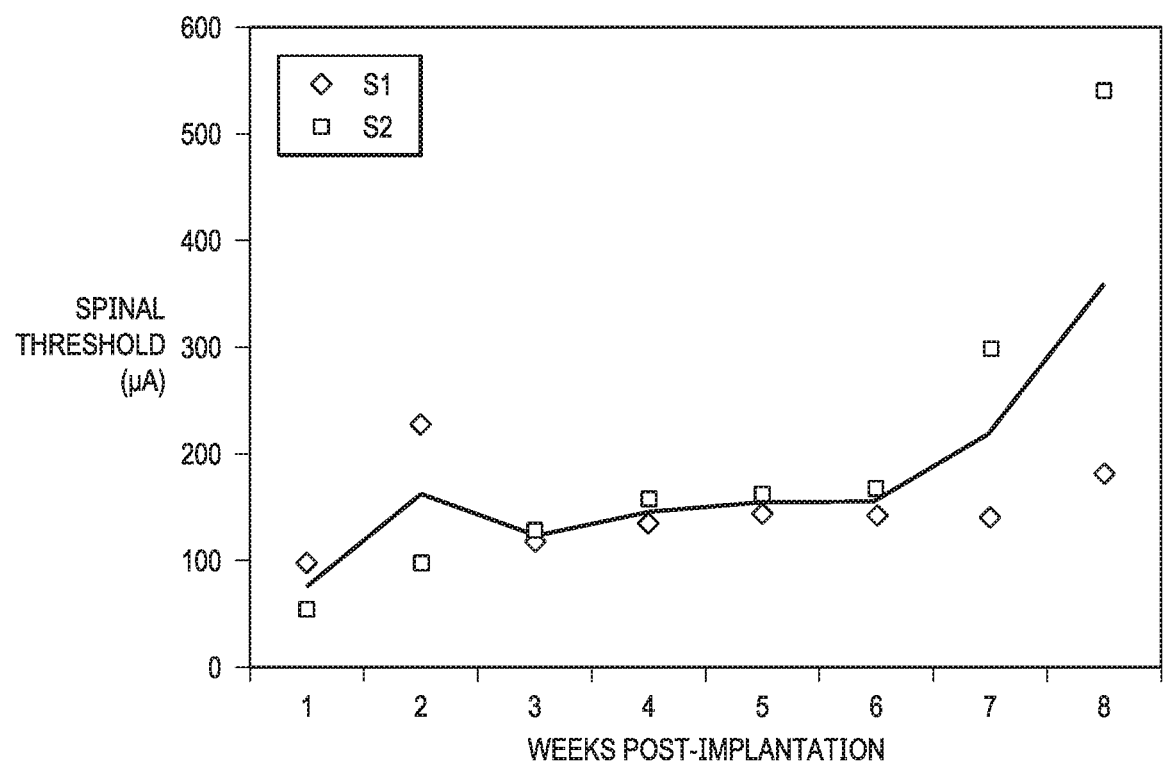

SPINAL CORD STIMULATOR DEVICE AND METHODS OF MANUFACTURE AND USE THEREOF

CROSS-REFERENCE TO RELATED APPLICATION

This application is the National Stage of, and therefore claims the benefit of, International Application No. PCT/US2017/058857 filed on Oct. 27, 2017, entitled "SPINAL CORD STIMULATOR DEVICE AND METHODS OF MANUFACTURE AND USE THEREOF," which was published in English under International Publication Number WO 2018/089215 on May 17, 2018; and claims priority to U.S. Provisional Application 62/420,814 filed Nov. 11, 2016, entitled "SPINAL CORD STIMULATOR DEVICE AND METHODS OF MANUFACTURE AND USE THEREOF,". The above application is commonly assigned with this National Stage application and is incorporated herein by reference in its entirety.

TECHNICAL FIELD

This application is directed, in general, to electrical devices, and more specifically, spinal cord stimulator devices, including methods of manufacturing and using such devices.

BACKGROUND

Electrical devices that can stimulate nerves in the spinal cord have the potential to improve the lives of patients suffering from pain and paralysis. Important technological barriers to overcome toward achieving such goals include the ability to provide spinal cord stimulating devices that can be implanted with a minimum of tissue damage during and after implantation, and, provide stable electrical potentials for nerve stimulation over chronic implantation periods (e.g., weeks or months).

SUMMARY

One embodiment can be a spinal cord stimulator device. Embodiments of the device can comprise an implantation paddle including at least one pair of electrode stimulation pads, each of the electrode stimulation pads connected to ends of separate thin film electrode leads, wherein the electrode stimulation pads and the thin film electrode leads are sandwiched between softening polymer layers. Embodiments of the device can comprise a connection segment, including insulated wire leads, one end of each of the wire leads can be connected to contact pads on opposite ends of each one of the thin film leads at separated coupling joints. Embodiments of the device can comprise an encapsulant encompassing portions of the implantation paddle, including encompassing portions of the softening polymer layers surrounding the contact pads, the coupling joints and portions of the connection segment including portions of the wire leads next to the coupling joints.

Another embodiment can be a method of manufacturing a spinal cord stimulator device. Embodiments of the method can comprise providing an implantation paddle, the implantation paddle including at least one pair of electrode stimulation pads, each of the electrode stimulation pads connected to ends of separate thin film electrode leads, wherein the electrode stimulation pads and the thin film electrode leads are sandwiched between softening polymer layers. Embodiments of the method can comprise connecting one end of insulated wire leads to contact pads of the opposite ends of each one of the thin film electrode leads by forming separated coupling joints. Embodiments of the method can comprise encompassing portions of the thin film electrode leads and portions of the insulated wire leads in the vicinity of the coupling joints with an encapsulant.

Another embodiment can be a method of spinal cord stimulation. Embodiments of the method can comprise passing the implantation paddle of the spinal cord stimulator device between two vertebrae of a spinal cord. Embodiments of the method can comprise inserting the implantation paddle into an epidural or a subdural space between the spinal cord and the vertebra, wherein a long axis of the implanted implantation paddle is aligned with a long dimension of the spinal cord, and after implantation, the two softening polymer layers soften and wrap around part of a circumference of the spinal cord. Embodiments of the method can comprise connecting ends of the wire leads to a voltage source. Embodiments of the method can comprise applying a voltage from the voltage source across the ends of the wire leads to generate an electric field between the pair of electrode pads.

BRIEF DESCRIPTION

The embodiments of the disclosure are best understood from the following detailed description, when read with the accompanying FIGUREs. Some features in the figures may be described as, for example, "top," "bottom," "vertical" or "lateral" for convenience in referring to those features. Such descriptions do not limit the orientation of such features with respect to the natural horizon or gravity. Various features may not be drawn to scale and may be arbitrarily increased or reduced in size for clarity of discussion. Reference is now made to the following descriptions taken in conjunction with the accompanying drawings, in which:

FIG. 1E shows a plan view of another example spinal cord stimulator device of the disclosure;

FIG. 1F shows a detailed plan view of part of the example spinal cord stimulator device shown in FIG. 1E;

Figure 2:
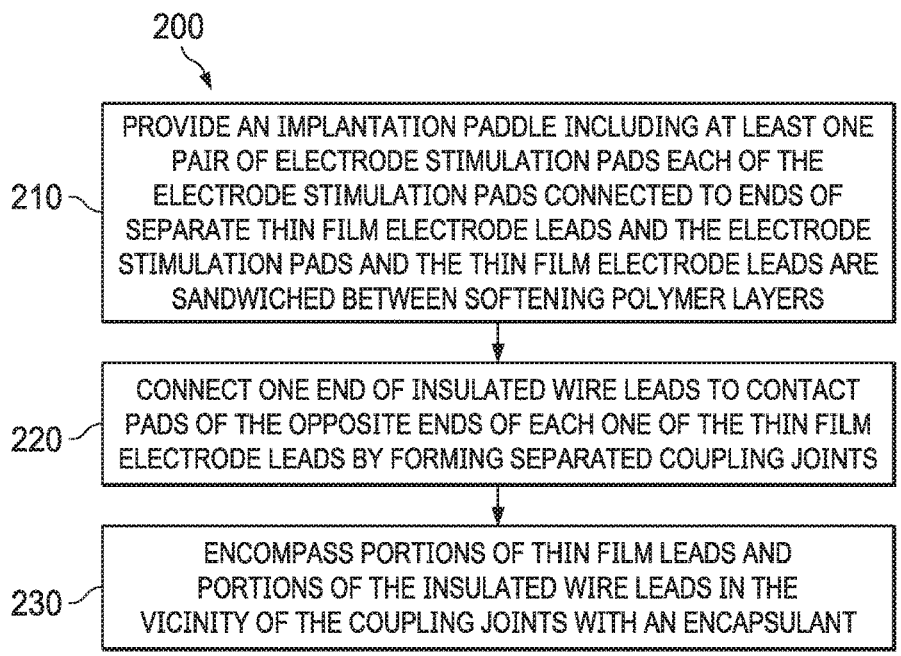
Figure 3:
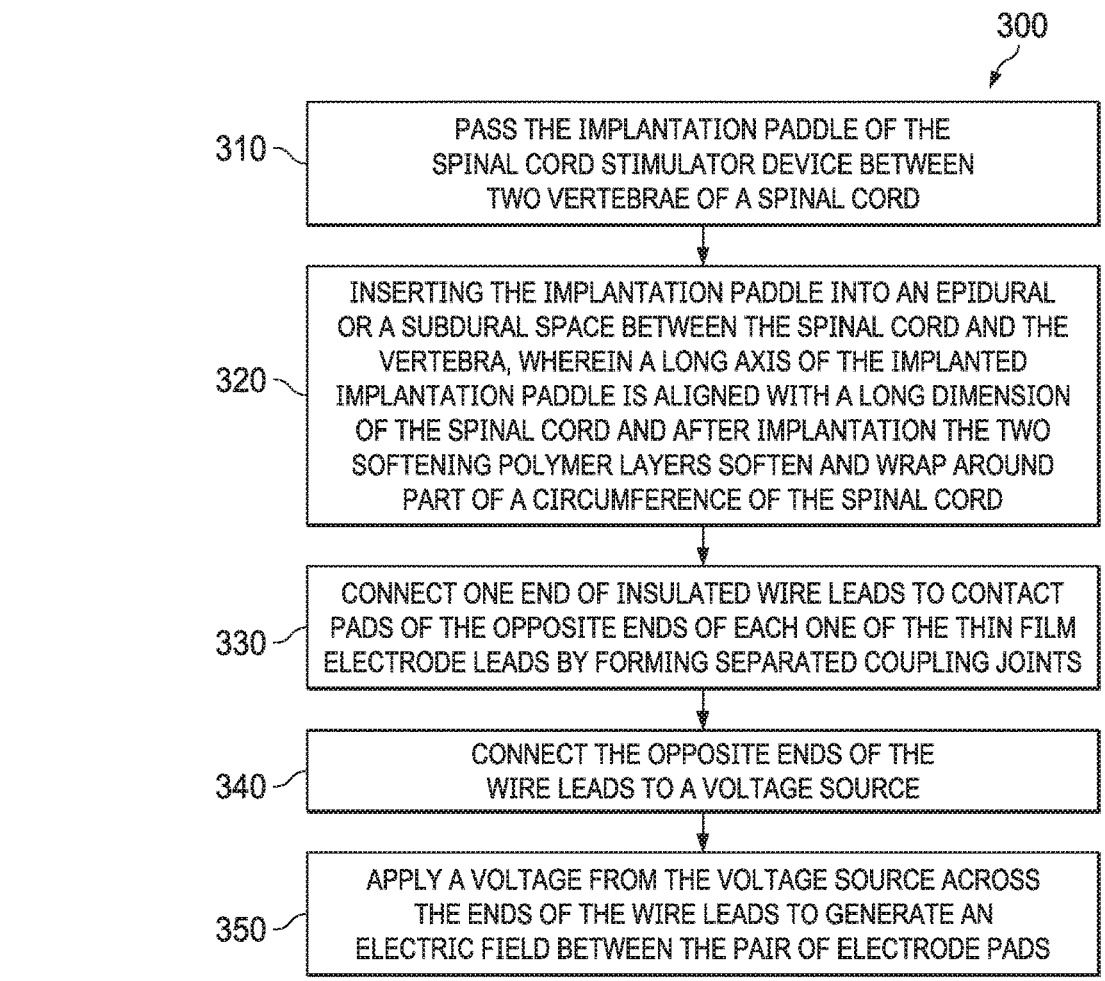
Figure 4A:
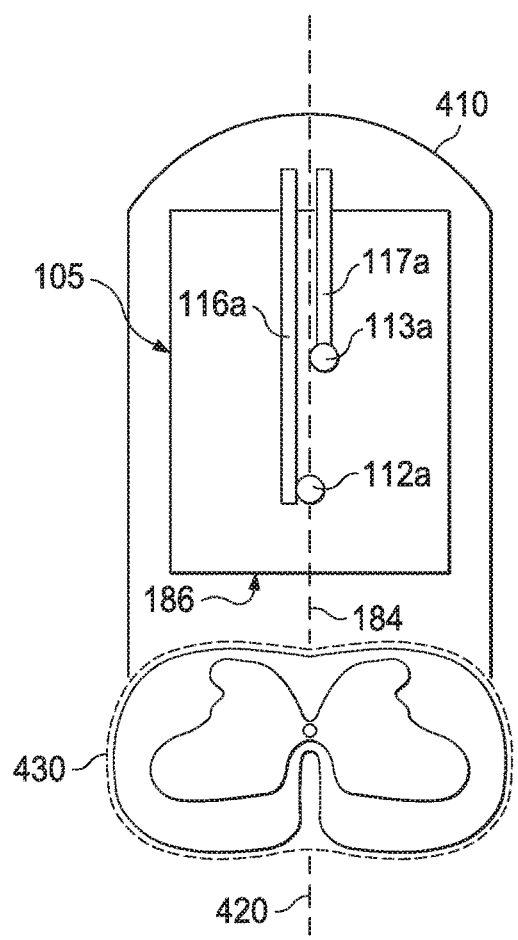
Figure 4B:
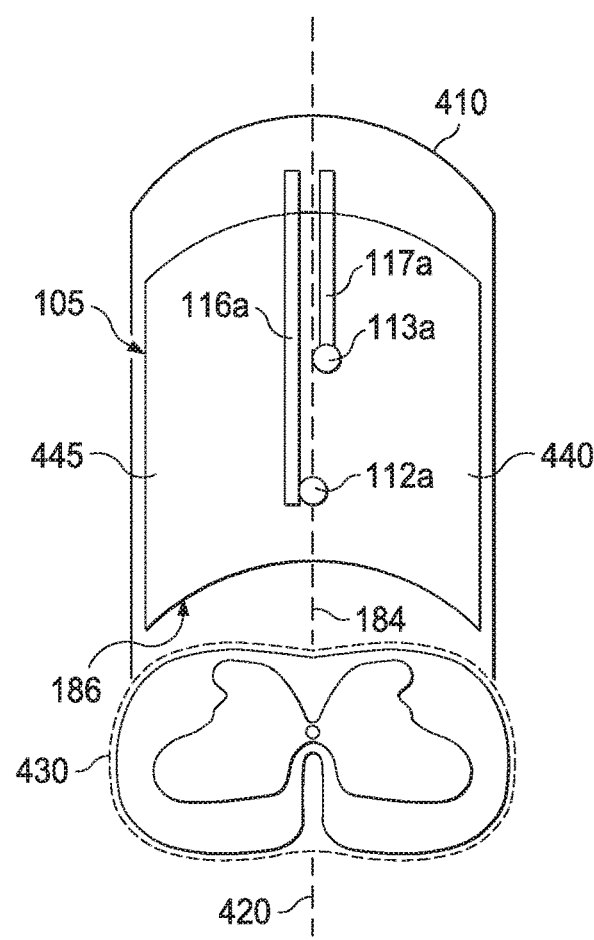
Figure 5A:
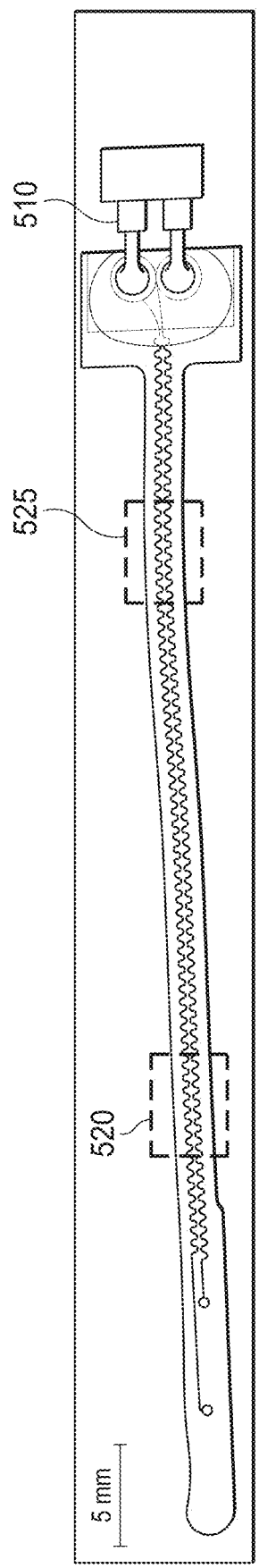
Figure 5B:
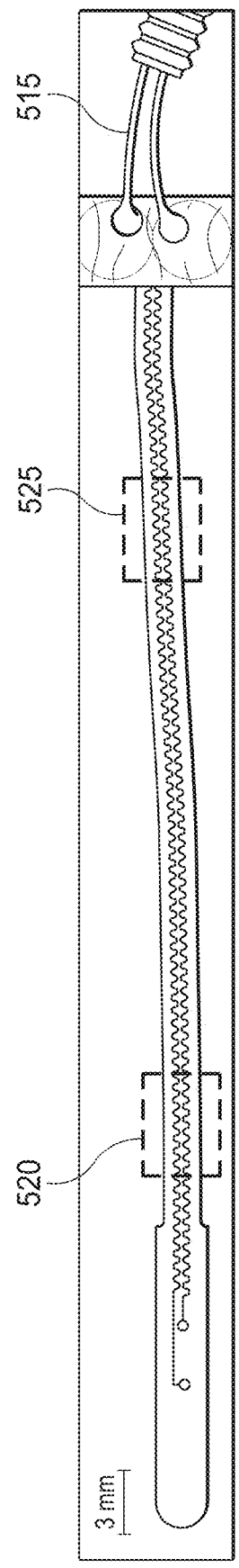
Figure 5C:
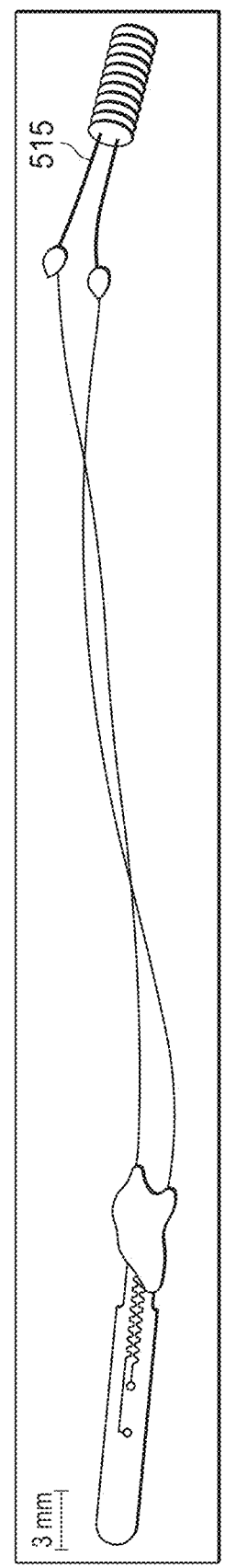
Figure 6A:
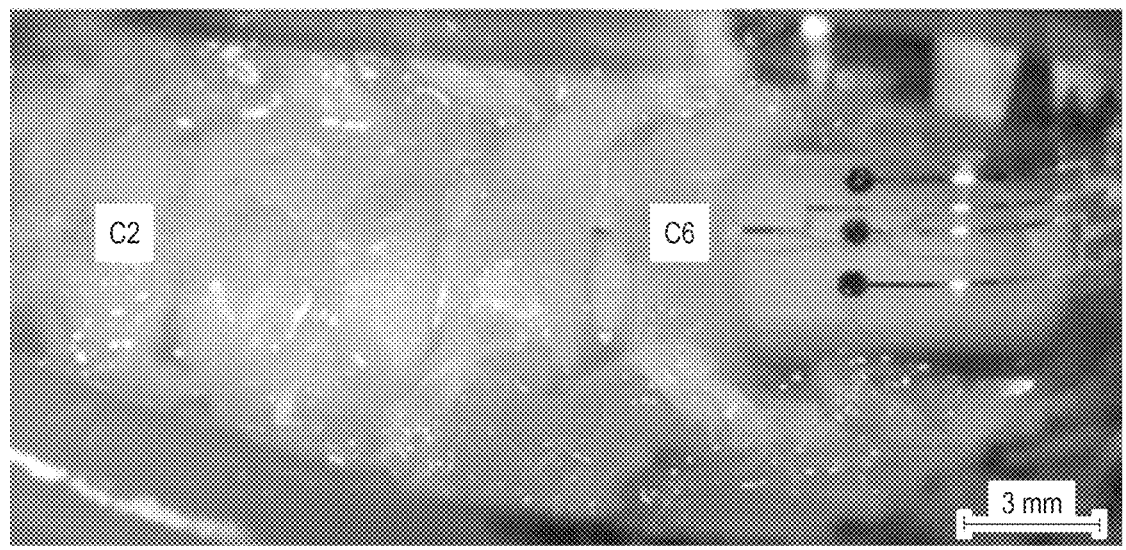
Figure 6B:
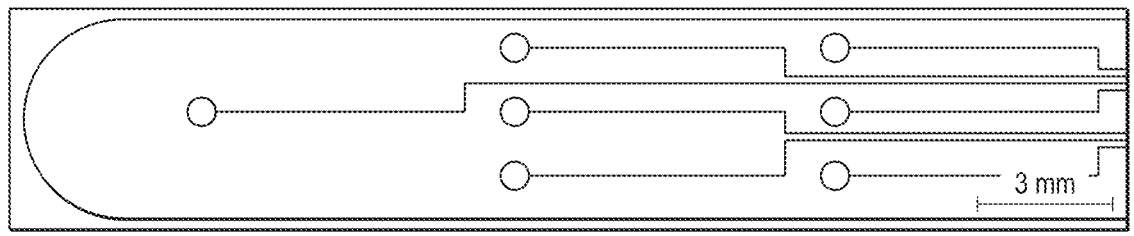
Figure 7A:
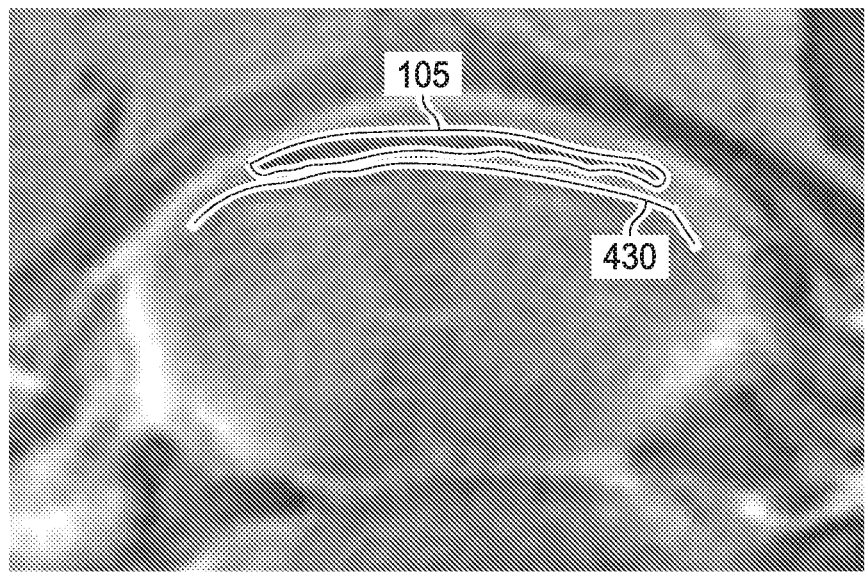
Figure 7B:
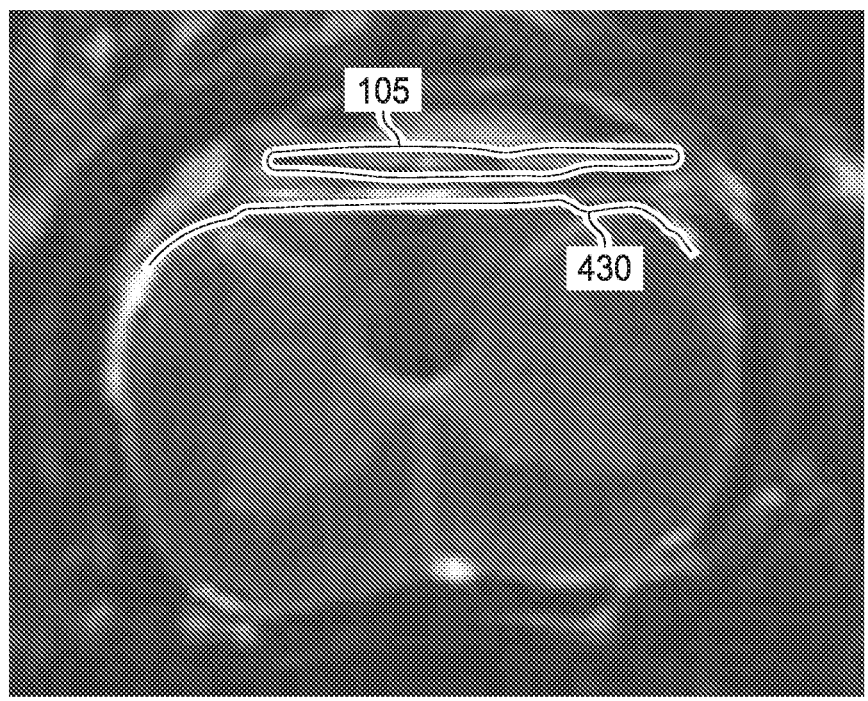
Figure 8A:
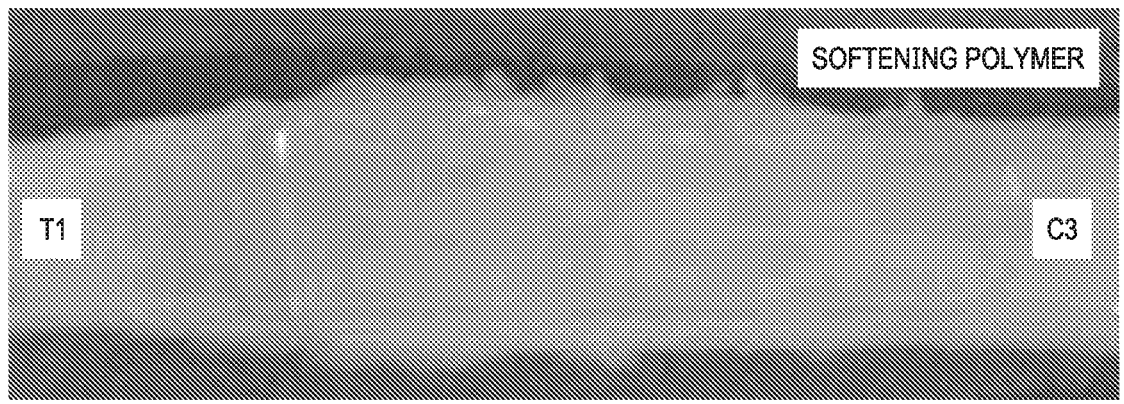
Figure 8B:
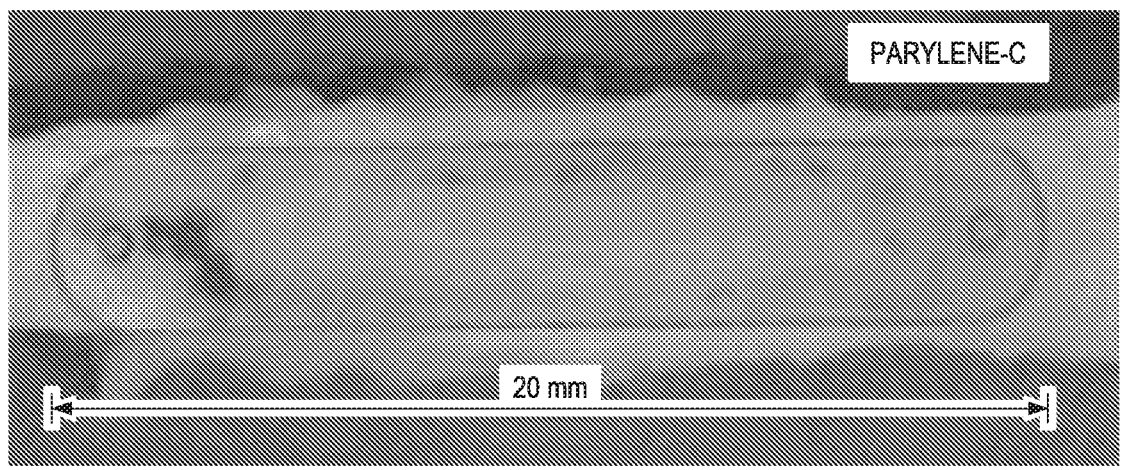
Figure 9:
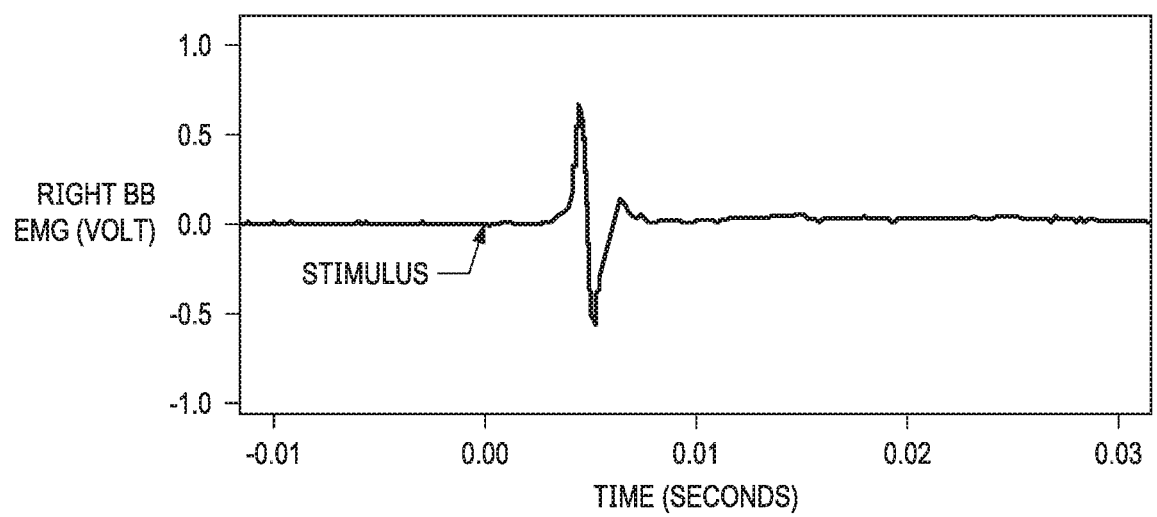
Figure 10:
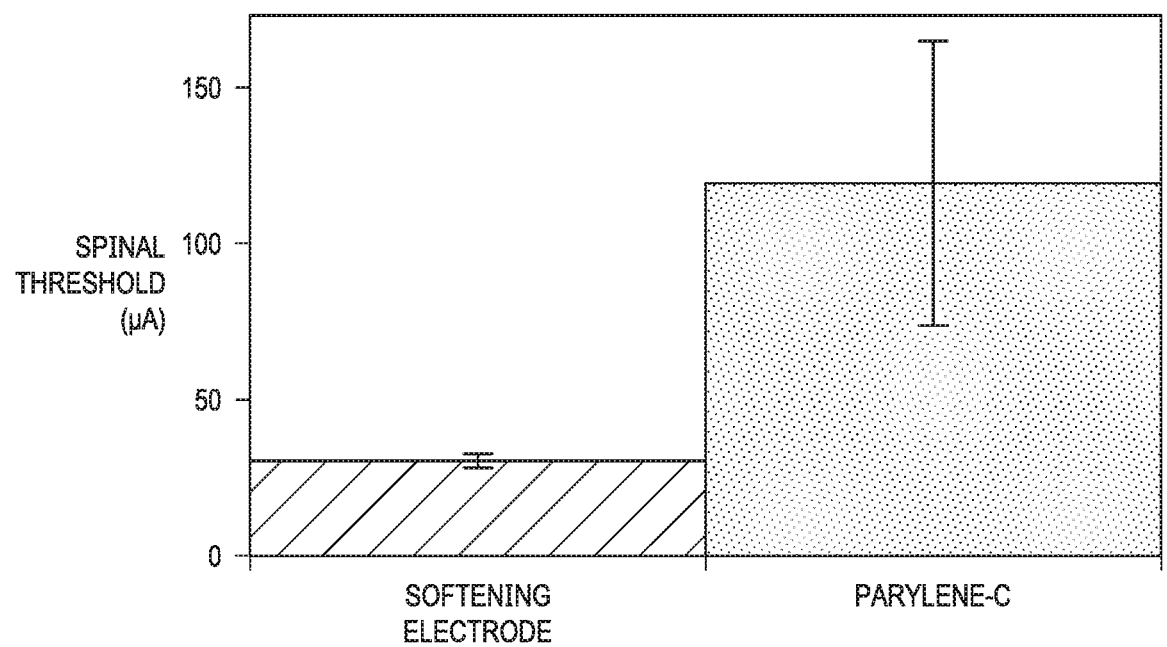
Figure 12A:
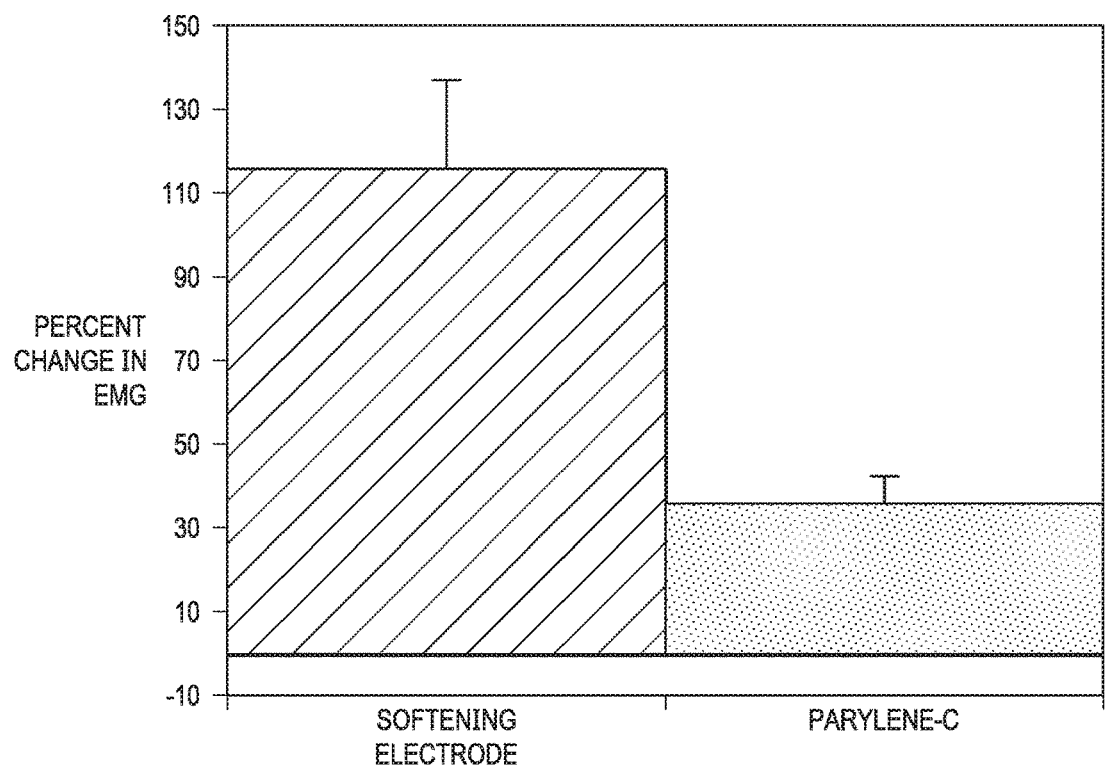
Figure 12B:
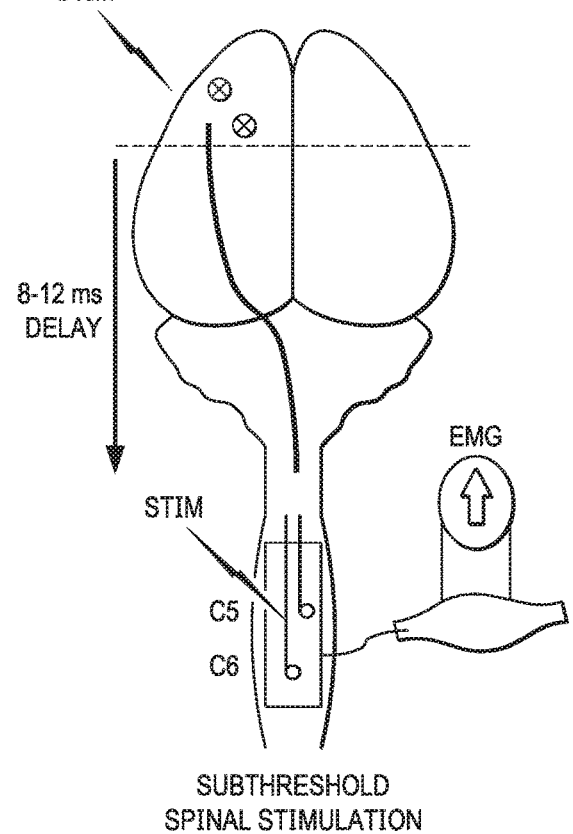
Figure 13A:
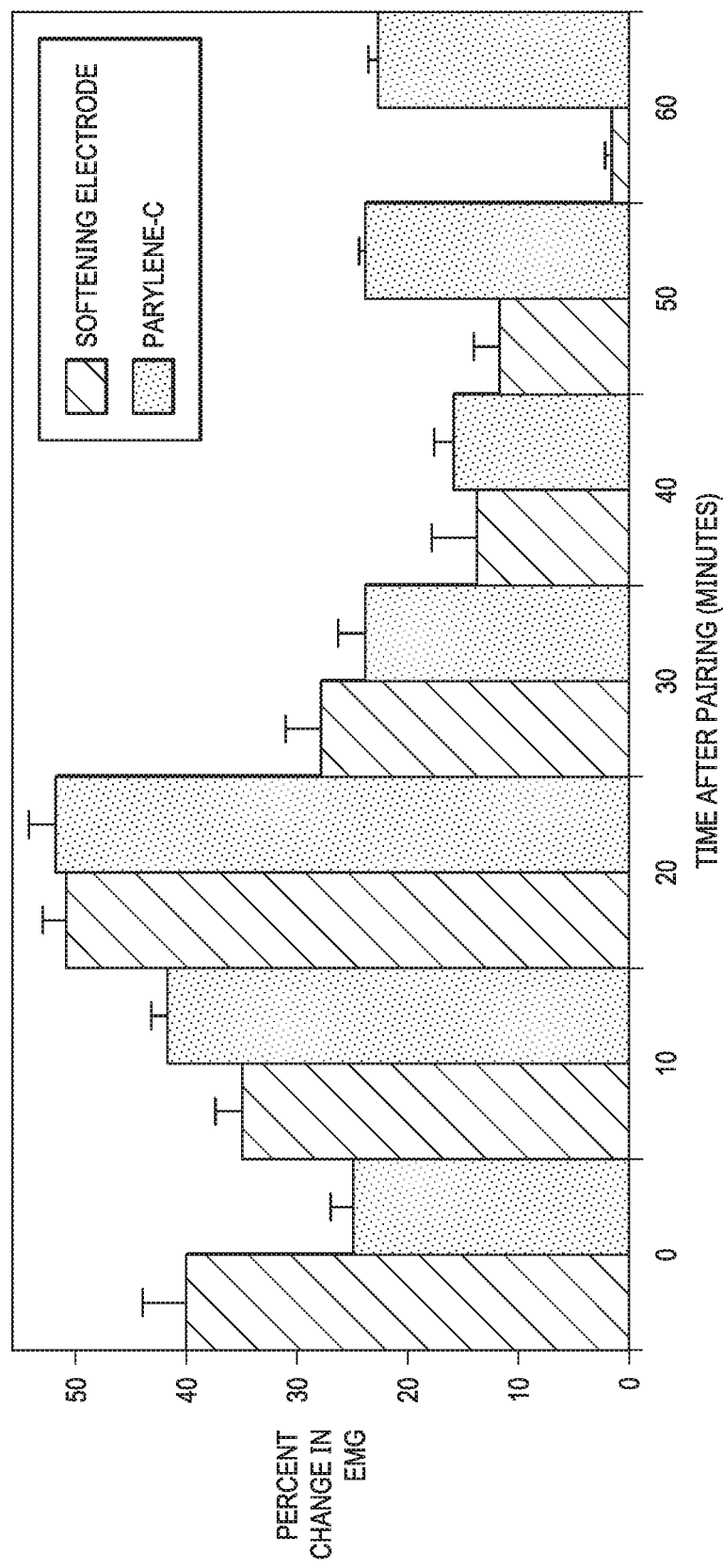
Figure 13B:
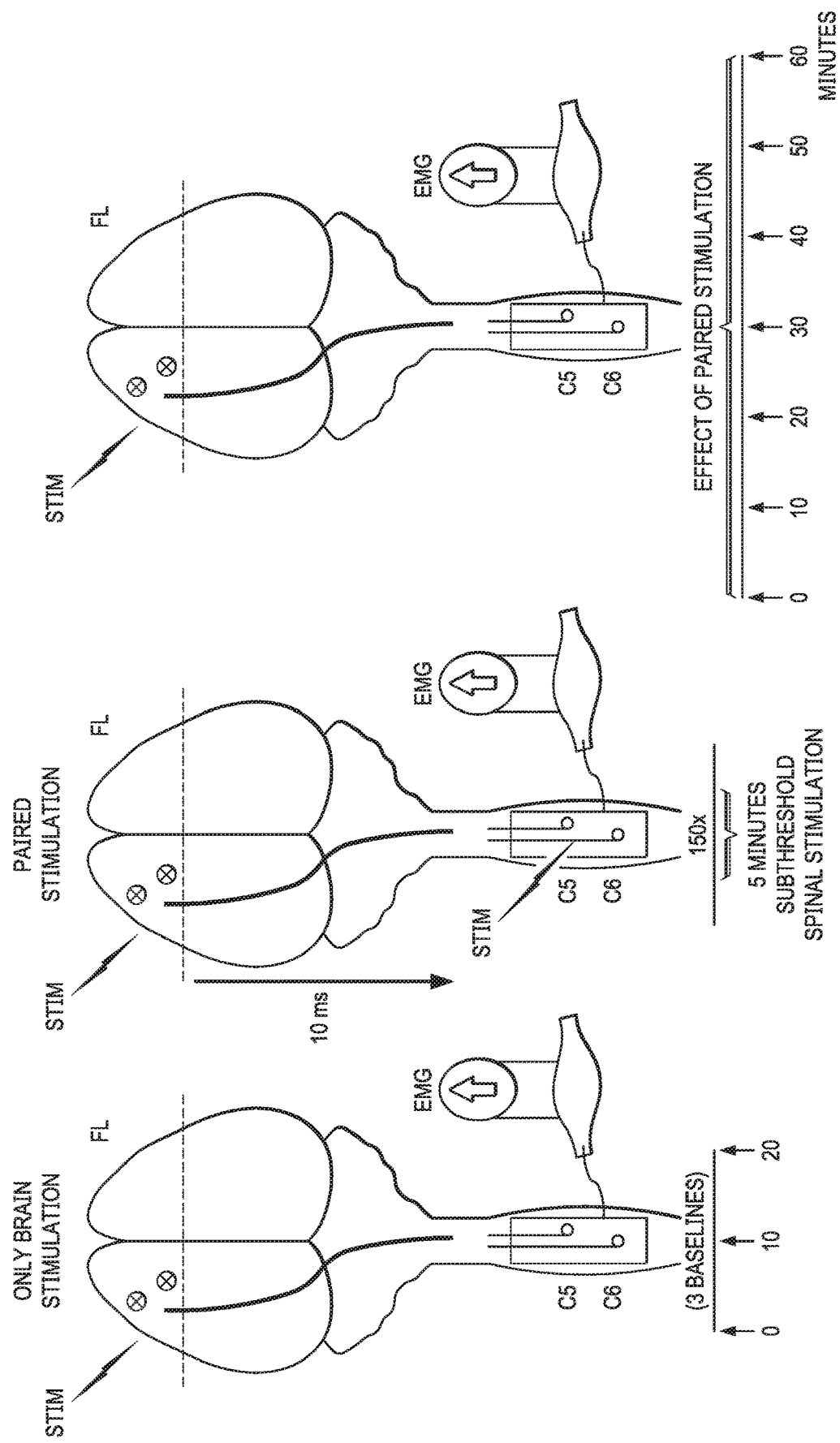

FIG. 2 presents a flow diagram of an example method of manufacturing spinal cord stimulator device such as any of the embodiments of the example spinal cord stimulator devices disclosed herein;

FIG. 3 presents a flow diagram of an example method of spinal cord stimulation, using any of the example spinal cord stimulator devices disclosed herein;

FIGS. 4A and 4B present perspective partial view sketches of an implantation paddle of the spinal cord stimulator device of the disclosure: (A) immediately after inserting the implantation paddle into an epidural or a subdural space between the spinal cord and the vertebra and (B) after a period time following implantation;

FIGS. 5A-5C present photographs of different spinal cord stimulator devices of the disclosure;

FIG. 6A shows a plan view photograph of an example spinal cord stimulator device of the disclosure during implantation under the C2 through C6 vertebra of a rat spinal cord;

FIG. 6B presents a plan view photograph of the example spinal cord stimulator device depicted in FIG. 6A prior to implantation;

FIGS. 7A and 7B present axial MRI views of implanted spinal cord stimulator devices of the disclosure three weeks after implantation adjacent to the spinal cords of rats the implantation paddles of the devices having: (A) softening polymer layers or (B) parylene-C layers;

FIGS. 8A and 8B show post-mortem anterior posterior photographs of portions of rat spinal cord one week post-implantation with dummy paddles having: (A) softening polymer layers or (B) parylene-C layers;

FIG. 9 presents an example electromyogram of the muscle response from a rat implanted with a spinal cord stimulator device of the disclosure when stimulated above a stimulation threshold in accordance with the disclosure;

FIG. 10 shows example spinal cord stimulation thresholds ("spinal threshold") to evoke a muscle response measured via electromyography, measured in rats implanted with spinal cord stimulator devices that include implantation paddles having softening polymer layers ("softening electrode") or parylene-C layers ("parylene-C"), respectively;

FIG. 11 shows spinal stimulation thresholds, generated similar to that described in the context of FIGS. 9-10, over time for rat subjects (S1, S2) implanted with spinal cord stimulator devices that include implantation paddles having softening polymer layers;

FIG. 12A shows example changes in the electromyogram measured muscle response ("percent change in EMG"), in rats implanted with spinal cord stimulator devices that include implantation paddles having softening polymer layers or parylene-C layers, respectively;

FIG. 12B presents a sketch illustrating aspects of a method of stimulating the spinal cord of rats implanted with spinal cord stimulator devices with paired brain and spinal cord sub-threshold stimulation to evoke the EMG responses such as depicted in FIG. 12A;

FIG. 13A presents example changes in the electromyogram measured muscle response ("percent change in EMG"), in rats implanted with spinal cord stimulator devices that include stimulating electrode portions having softening polymer layers ("softening electrode") or parylene-C layers ("paralene-C"), respectively, for different times after paired brain and spinal cord sub-threshold stimulation; and FIG. 13B presents a sketch illustrating aspects of methods of stimulating the spinal cord of rats implanted with spinal cord stimulator devices with paired brain and spinal cord sub-threshold stimulation to evoke the EMG responses such as depicted in FIG. 13A.

DETAILED DESCRIPTION

The spinal cord stimulating devices disclosed herein have a combination of design features conducive to chronic spinal implantation. The softening polymer layers of an implantation paddle portion of the device are rigid enough to allow implantation of the paddle into the epidural or subdural space between the spinal cord and vertebra without buckling or bending the paddle during implantation. As disclosed herein the paddle is thin and has a width:length aspect ratio that is conducive to implantation while still minimizing tissue damage.

The softening polymer layers of the paddle, once implanted, substantially soften (e.g. an order of magnitude or more decrease in elastic modulus) thereby reducing the likelihood of chronic tissue damage. Additionally, softening facilitates the implantation paddle hugging the dura without excessive force on the spinal cord. We believe that such an arrangement helps reduce stimulation electrode lead migration as compared to paddles composed of material that stays rigid after implantation. Surprisingly, the implanted thin softening polymer layers of the paddle are able to withstand the mechanical force exerted inside the epidural or subdural space.

We believe that these features are in contrast to and non-obvious in view of certain conventional spinal cord stimulating devices which have been designed to be thick and rigid so as to facilitate implantation and withstand the mechanical forces associated with spinal cord bending, twisting and stretching. Such conventional spinal cord stimulating devices retain their rigidity after implantation and often have larger thickness dimensions than the devices disclosed herein. Due to their continued rigidity after implantation, such devices tend not to hug the dura of the naturally curved circumference of the spinal cord. Consequently, such rigid devices can deform and cause tissue damage to the spinal cord in the vicinity of implantation. Moreover, over time, the stimulation electrodes of such rigid devices tend to migrate away from their originally implanted location thereby changing the electrical potential required for nerve stimulation.

These features are also in contrast and non-obvious in view of certain conventional spinal cord stimulating devices that include soft paddle materials, e.g., silicone, which can be difficult to implant into the epidural or subdural space without buckling or bending.

Additionally, as disclosed herein, to reduce the possibility of shearing damage to the softening polymer layer, embodiments of the implantation paddle can be limited to a length that can substantially fully implanted in the epidural or subdural space and lay parallel to target portion of the spinal cord to be stimulated. While not limiting the scope of the disclosure by theoretical considerations, we believe that such implantation paddles are subject to a lesser number and/or lower severity of mechanical forces associated with back or neck movement, e.g., as compared to a paddle length where substantial portions of the paddle reside outside of the epidural or subdural space.

We have discovered, as disclosed herein, that the mechanical forces associated with back and neck movement are better tolerated by a connection segment of the device that includes insulated wire leads that are connected to thin film leads of the implantation paddle. Such insulated wire leads extending up between vertebra are more tolerant to the large mechanical forces associated with back and neck movement that can occur. The coupling joints between the wire leads and thin film leads can be surrounded by an encapsulant as disclosed herein to mitigate against breakage of the joints, e.g., due to back and neck movement.

Consequently, embodiments of the spinal cord stimulator device disclosed herein can be implanted with a minimum of tissue damage during and after implantation, and, provide stable electrical potentials for nerve stimulation over chronic implantation periods (e.g., weeks or months).

One embodiment of the disclosure is a spinal cord stimulator device.

Figure 1A:
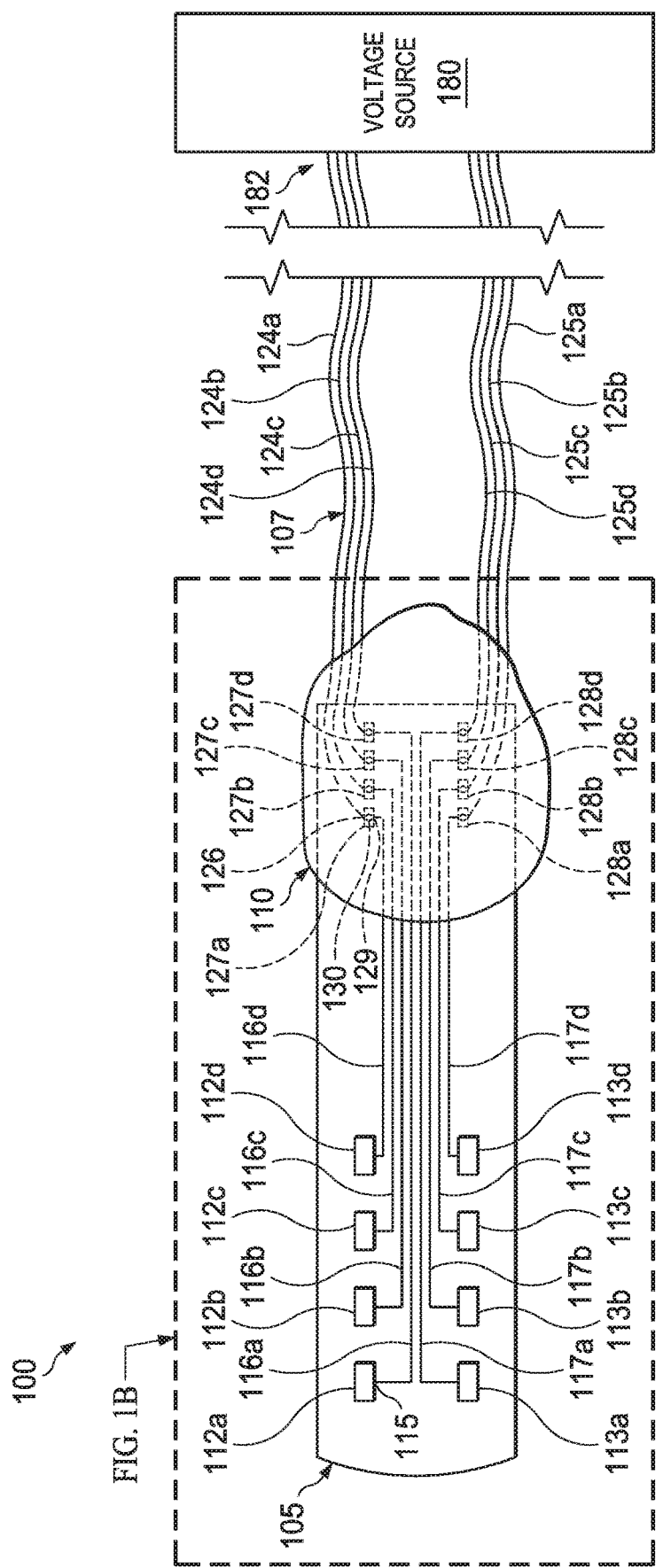
FIG. 1A shows a plan view of an example spinal cord stimulator device of the disclosure.
Figure 1B:
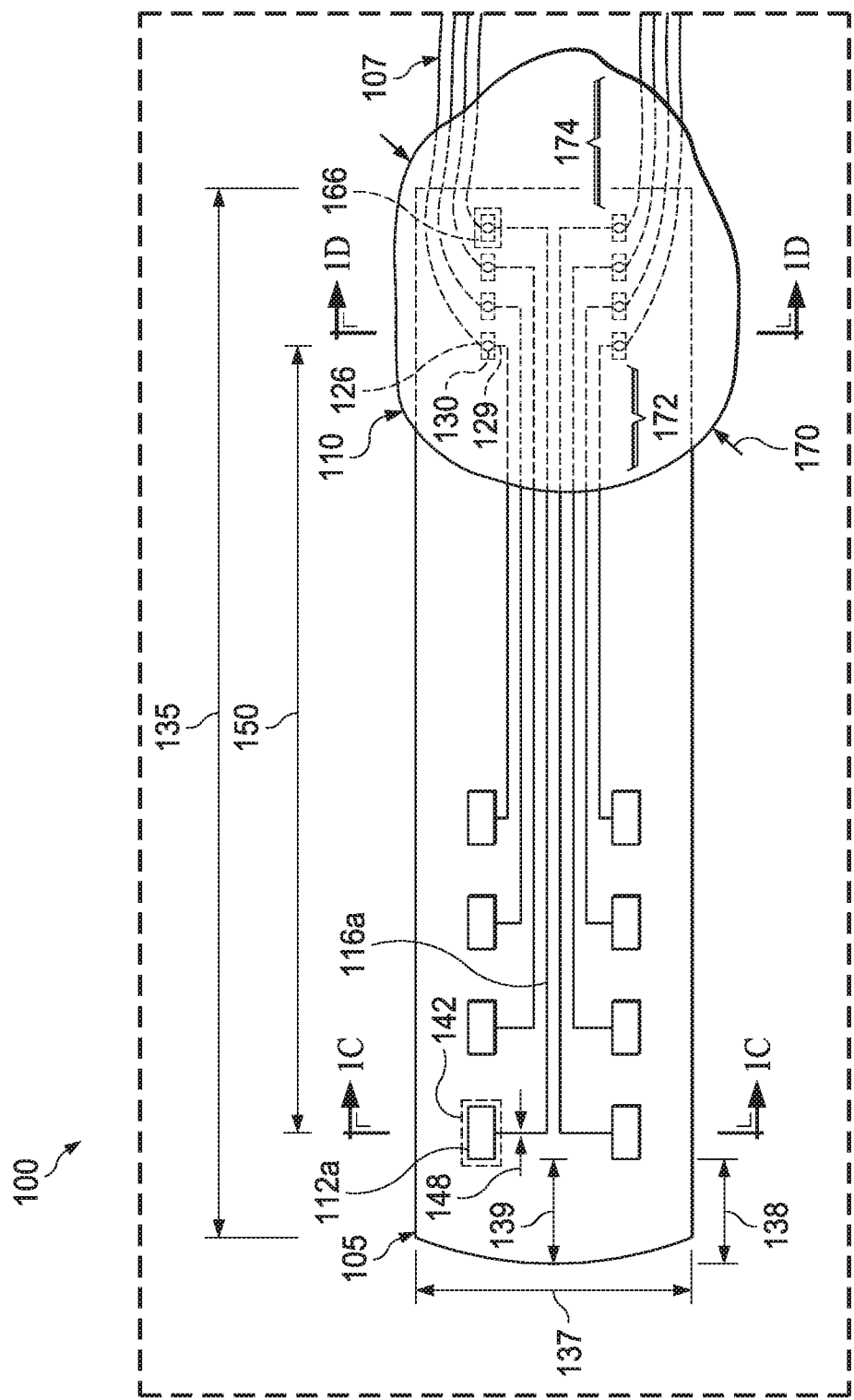
FIG. 1B shows a detailed plan view of part of the example spinal cord stimulator device shown in FIG. 1A.
Figure 1C:
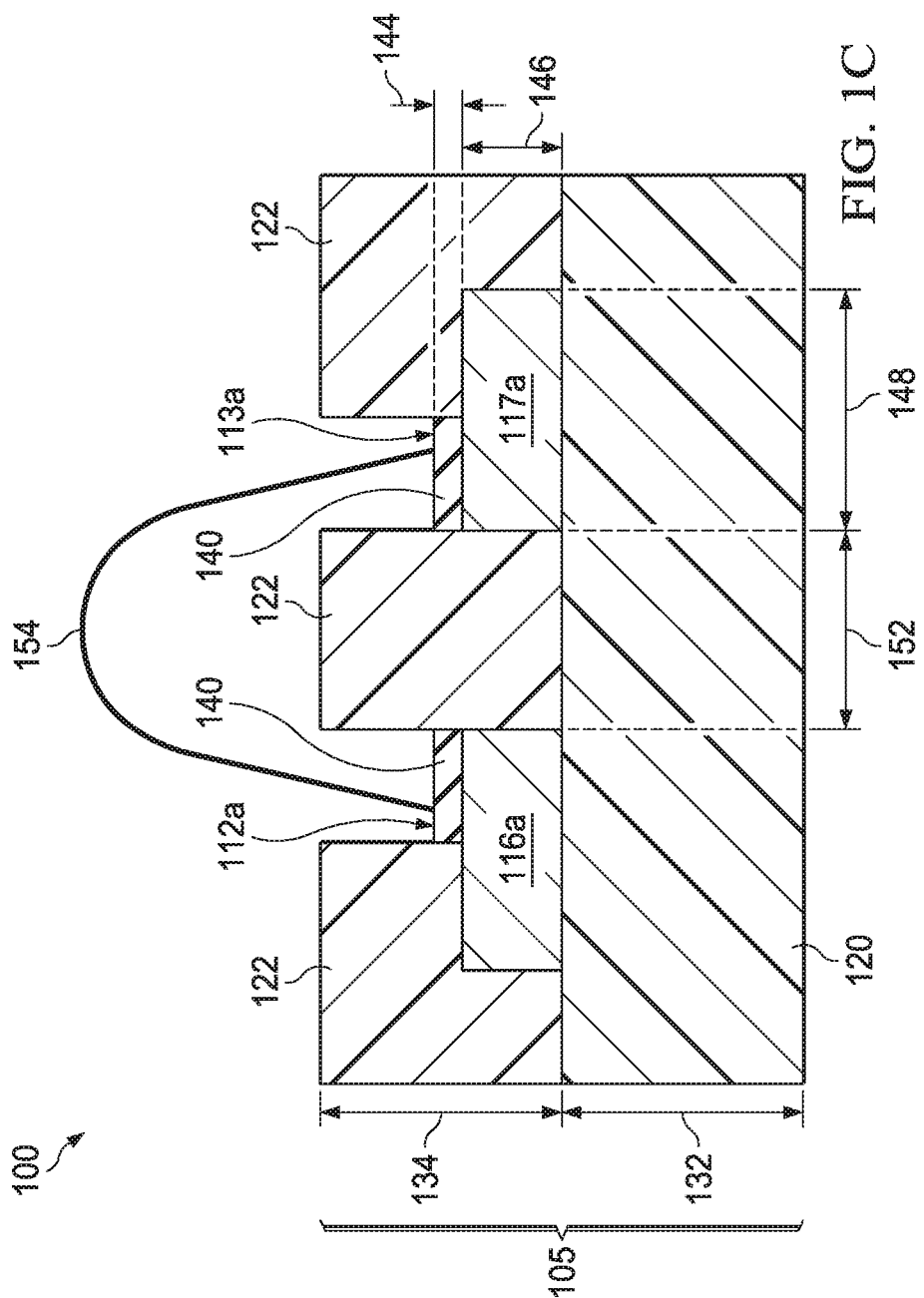
FIG. 1C shows a cross-sectional view of the example spinal cord stimulator device shown in FIG. 1A, along view line 1C-1C as depicted in FIG. 1B.
Figure 1D:
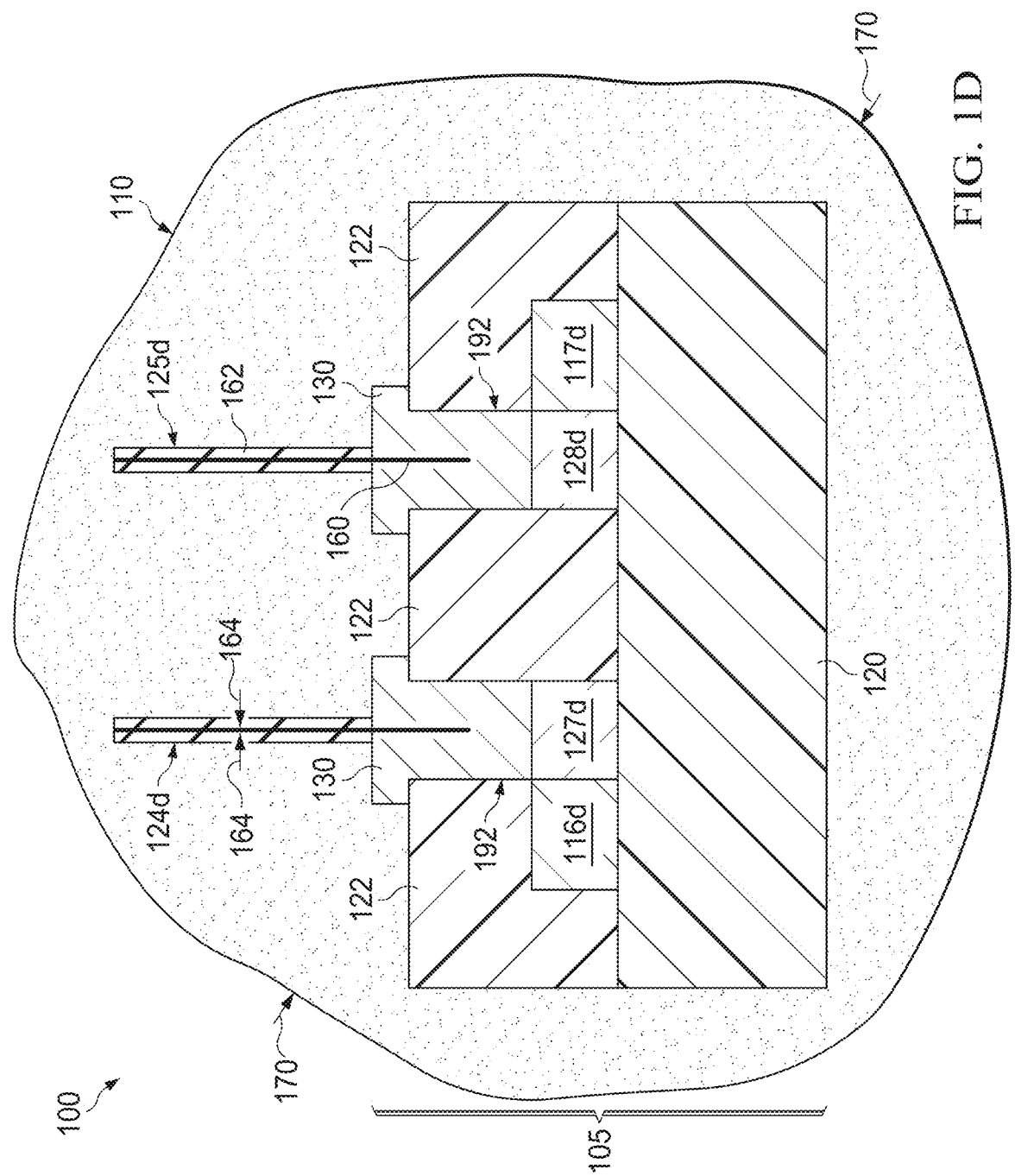
FIG. 1D shows a cross-sectional view of the example spinal cord stimulator device shown in FIG. 1A, along view line 1D-1D as depicted in FIG. 1B.

FIG. 1A shows a plan view of an example spinal cord stimulator device 100 of the disclosure and FIG. 1B shows a detailed plan view of part of the example spinal cord stimulator device 100 shown in FIG. 1A. FIGS. 1C and 1D show cross-sectional views of the example spinal cord stimulator device 100 shown in FIG. 1A along view lines 1C-1C and 1D-1D, respectively, as depicted in FIG. 1B.

With continuing reference to FIGS. 1A-1D throughout, embodiments of the device 100 can comprise an implantation paddle 105, a connection segment 107 and an encapsulant 110. The implantation paddle 105 can include at least one pair of electrode stimulation pads (e.g., pads 112a, . . . and pads 113a, . . . ), each of the electrode stimulation pads connected to ends (e.g., end 115) of separate thin film electrode leads (e.g., leads 116a, . . . , and leads 117a, 117b, 117c, . . . ). As illustrated in FIGS. 1C and 1D, the electrode stimulation pads (e.g., pads 112a and 113a) and the thin film electrode leads (e.g., thin film leads 116a and 117a can be sandwiched between softening polymer layers (e.g., layers 120, 122).

The connection segment 107 can include insulated wire leads (e.g., wire leads 124a, . . . and wire leads 125a, . . . ). One end (e.g., end 126) of each of the wire leads is connected to contact pads (e.g., contact pads 127a, . . . and contact pads 128a, . . . ) on opposite ends (e.g., end 129) of each one of the thin film leads at separated coupling joints 130 (e.g., each coupling joint separated from all other coupling joints).

The encapsulant 110 can encompass portions of the implantation paddle 105, including portions of the softening polymer layers 120, 122 surrounding the contact pads contact pads 127a, the coupling joints 130, and, encompassing portions of the connection portion 107 include portions of the wire leads 124a . . . , 125a, . . . next to the coupling joints 130.

As noted above, the softening polymer layers 120, 122 are more rigid under ex vivo pre-implantation conditions (e.g., room temperature and air environment) than under in vivo implanted conditions (e.g., 37° C. and aqueous environment). For example, embodiments of the softening polymer layers 120, 122 can be composed of a polymer, designated SMP6, formed from a stoichiometric combination of the monomers Tris[2-(3-mercaptopropionyloxy)ethyl] isocyanurate (TMICN) and 1,3,5-triallyl-1,2,5-triazine-2,4,6 (1H, 3H,5H)-trione (TATATO) combined with 31 mol % Tricyclo [$5.2.1.0^{2,6}$]decanedimethanol diacrylate (TCMDA) polymerized in the presence of the photocuring agent 2,2-Dimethoxy-2-phenylacetophenone. Layers of SMP6 can have an elastic modulus of about 1.8 GPa at 21° C. and air environment. After about 5 hours in water at 37° C., the elastic modulus drops by nearly two orders of magnitude to about 50 MPa.

Other embodiments of the softening polymer layers can be composed of polymers formed from combinations of monomers functionalized with thiol-enes, thiol-ene or acrylates) can have a glassy modulus of 1-3 GPa (e.g., at room temperature in air) and exhibit a rubbery plateau in modulus (e.g., at 37° C. in water) that can range from 100 MPa down to as low as 0.03 MPa, which is at or below the modulus of tissue.

As illustrated in FIG. 1C, to maintain sufficient paddle rigidity pre-implantation and toughness during implantation, embodiments of the softening polymer layers 120, 122 can have a thickness 132, 134 in a range from 20 to 100 microns, e.g., about 25, 50 or 75 microns in some embodiments. Having about a same thickness 132, 134 can facilitate placing the pads 112a, . . . 113a . . . and the thin film electrode leads 116a, . . . , 117a, . . . at or near a mechanical neutral plane of the implantation paddle 105 and thereby help prevent delamination of these pads and leads from the soften layer 132, e.g., when the paddle 105 is bent during and/or following implantation.

Embodiments of the spinal cord implantation paddle 105 can have a long and narrow aspect ratio to facilitate implantation in the epidural space. For example, in some embodiments as illustrated in FIG. 1B, a width 137 to long axis length 135 aspect ratio can range from 1:6 to 1:8. For example, in some embodiments, when the length 135 of the paddle 105 equals 130 mm or 65 mm the paddle's width 137 can equal 20 mm or 10 mm, respectively. For example, in some embodiments, when the length 135 of the paddle 105 equals 15 mm, the paddle's width 137 can equal 2 mm.

In some embodiments, to facilitate having the implanted paddle 105 to wrap around and hug a target portion of the spinal cord dura or spinal cord subdurally, the width 137 of the paddle 105 can be in a range from 5 to 30 percent of the circumference of the spine. For example, when the target portion of the human spine has an average diameter (e.g., average of transverse and anteroposterior diameters) of about 10 mm, then the circumference equals about 31 mm, and for a paddle width 137 equal to 10 mm, the paddle wraps around about 31 percent of the circumference of the spinal cord. Of course, other factors, such as the number and distribution of electrode stimulation pads 112a, . . . , 113a, . . . and thin film electrode leads 116a, . . . 117a, . . . , can also affect the minimum width 137 dimensions of the paddle 105.

As illustrated in FIG. 1B, to facilitate implantation, some embodiments of the paddle 105 can have a leading segment 138 that includes the softening polymer layers 120, 122 and is free of the electrode stimulation pads 112a, . . . 113a, . . . and the thin film traces 116a, . . . 117a, . . . . Providing such a leading segment 138, free of electronic components, allows bending of the segment 138 at large angles (e.g., greater than 90 degree angles) to facilitate placing the paddle under vertebra in the epidural or subdural space while mitigating the risk of breaking or delaminating the pads or traces from the softening polymer layers during such implantation maneuvers. For example, in some embodiments the leading segment 138 can have a length 139 (e.g., from a curved leading edge of the paddle 105 to the edge of the most forward located pads 112a, 113a) in a range from 5 mm to 20 mm.

As illustrated in FIG. 1C, some embodiments of the electrode stimulation pads (e.g., pad 112a) can include a titanium nitride layer 140 deposited (e.g., sputter deposited) on a portion of the thin film layer 116a, e.g., to facilitate producing a large charge injection capacity, which in turn, can facilitate nerve stimulation via a capacitive stimulation mechanism well understood by those skilled in the pertinent art. To facilitate the ability to carry sufficient current to generate a large charge injection density for such spinal nerve stimulation, embodiments of the electrode stimulation pads 112a can have a area perimeter 142 (FIG. 1B) in a range from about 2 $mm^2$ to 6 $mm^2$ (e.g., about 2 mm×3 mm) and can have a thickness 144 (FIG. 1C) in a range from about 5 to 2000 nanometers.

As illustrated in FIG. 1C, facilitate the ability to carry sufficient current, some embodiments of the thin film leads can be composed of gold deposited on the softening polymer layer having a thickness 146 in a range from about 100 to 5000 nanometers.

Other embodiments of thin film leads can be composed of copper, nickel, aluminum, platinum, PEDOT, carbon nanotubes, graphene, ultrananocrystalline diamond, chromium, alloys of several materials including palladium/nickel/gold.

As illustrated in FIG. 1B, in some embodiments, each of the thin film leads (e.g., lead 116a) can be rectilinear structures each having a width 148 in a range from 20 to 200 microns and length 150 (FIG. 1B) sufficient to place the contact pads under the targeted portion of the spinal cord. For example, in some embodiments, the thin film leads can range in length 150 from about 1 to 15 cm, e.g., so as to extend along an about 1 to 15 cm length portion of the long dimension of the spinal cord (e.g., any portion of the length of the spinal cord extending from the foramen magnum to the upper part of the lumbar region).

In some embodiments, the paired electrode stimulation pads (e.g., pads 112a and 113a), are configured as positive and negative voltage leads, respectively, to generate the nerve stimulating electric field. Embodiments of the paired electrode pads 112a, 113a can be separated a sufficient distance (e.g., edge-to-edge distance 152) to facilitate generating an electric field (e.g., comprising field line 154) that can penetrate into the spinal cord and thereby stimulate the targeted nerves of the spinal cord. For example, in some embodiments, the edge-to-edge distance 152 is in a range from about 1 to 10 mm, and in some embodiments about 2 to 5 mm.

FIGS. 1A and 1B depict an example device 100 embodiment having 8 electrode stimulation pads (e.g., four pairs of pads) and associated separate thin film electrode leads and wire leads. Based upon the present disclosure, one skilled in the pertinent art would understand how similar devices 100 could be constructed with 16, 32, 64, etc . . . , stimulation pads and associated separate thin film electrode leads and wire leads.

Yet other embodiments include devices 100 that can be fabricated with backplanes that allow a limited number of traces to address more than 4 electrodes, such as 16, 32, 64, 128, 256, 512, 1024, 2048, 4096, 8192 or more than 10,000 electrodes or some other number of electrodes that are addressed in this way.

As illustrated in FIG. 1D, embodiments of the wire leads 124a, . . . , 125a, . . . of the connection segment 107 can include a cylindrical wire 160 surrounded by an insulator layer 162. In some embodiments, for example, the cylindrical wire 160 can be composed of steel (e.g., stainless steel) and have a diameter 164 in a range from 25 to 50 microns). In some embodiments, for example, the insulator layer 162 can be composed of a non-electrically conducting polymer such as parylene-C, polyether ether ketone, polyimide and the like.

As illustrated in FIG. 1D, the coupling joints 130 can lay on the contact pad (e.g., contact pads 127a, 128a) and portions of the thin film electrode leads (e.g., leads 116a, 117a). To provide a bonding base for the wire 160, some embodiments of the contact pads 127a have a perimeter (e.g., perimeter 166, FIG. 1B) of with an area in a range from about 700 to 3000 microns. In some embodiments a portion of the wire 160 (e.g., removed of insulator layer 162) of the wire lead 124a, . . . , 125a, . . . can be inserted into, and bonded to, a solder paste of the coupling joint 130, e.g., via a melt-reflow process. Some embodiments of the coupling joint 130 can include a lead-free (e.g., less than about 0.1% lead) solder paste such an indium silver solder paste.

As illustrated in FIGS. 1B and 1D, to mitigate breakage of the coupling joints 130, some embodiments of the encapsulant 110 encompass the implantation paddle 105 around and portions of the thin film leads 116a, . . . 117a, . . . and the insulated wire leads 124a, . . . 125a, . . . , in the vicinity of the coupling joints 130. For example, some embodiments of the encapsulant 110 can have a substantially spherical shape with an average diameter 170 in a range of from about 1 to 10 mm. For example, a 1 mm diameter 170 droplet of the encapsulant 110, may be applied in the vicinity of the coupling joints 130 such that about 0.4 mm lengths 172 of the paddle 105 around the thin film leads and about 0.4 mm lengths around of the insulated wire leads are surrounded by the encapsulant 110. For example, a 6 mm diameter 170 droplet of the encapsulant 110, can be applied in the vicinity of the coupling joints 130 such that about 2.5 mm lengths 172 of the paddle 105 around the thin film leads and about 2.5 mm lengths around the insulated wire leads are surrounded by the encapsulant 110.

Some embodiments of the encapsulant 110 are composed of a silicone epoxy polymer.

As illustrated in FIG. 1A, some embodiments of the device 100 can further include a voltage source 180. Opposite ends (e.g., end 182) of the wire leads 124a, . . . 125a, . . . can be connected the voltage source 180. One skilled in the pertinent art would understand how the ends 182 of the wire leads 124a, . . . 125a, . . . could to be fashioned with connectors (e.g., pins) to interface with the voltage source 180.

The voltage source 180 can be configured to apply separate voltage potentials between any pair of the electrode stimulation pads (e.g., paired pads 112s, 113a). In some embodiments, the voltage source 180 can be implanted, e.g., under the skin, while in other embodiments the voltage source 180 can be outside of the body of the subject implanted with the implantation paddle 105 and ends 182 of the wire leads of the connection segment 107 can connect to the voltage source 180 outside of the body.

One skilled in the pertinent art would be familiar with how to configure the voltage source 180 as a pulse generator to generate repeating pulses of positive or negative voltage potential across the pairs of electrodes at a frequency from 20 to 120 Hz, and in some embodiment 50 to 60 Hz, or, in some embodiments, greater than 6 kHz, e.g., to facilitate nerve blocking, or, to mitigate pain associated with sciatica or other forms of chronic or acute pain.

Some embodiments of the voltage source 180 can be configured to generate and apply such voltage pulses to produce currents through the lead wires and the thin film electrode leads connected to the paired electrode pads, up to 26 mA over a range of voltages up to ±16 volts. In some such embodiments, the voltage pulses can be applied for durations (e.g., a pulse width) in a range of about 100 to 500 microsecond.

To mitigate tissue heating and damage, some embodiments of the voltage source 180 can be configured to generate and apply a biphasic pulse such that the positive and negative potentials across paired electrode stimulation pads alternately reverse. Some embodiments of the voltage source 180 can be configured to have a pulse-free interval between pulse, e.g., to allow a capacitive discharge of the stimulated tissue between pulses. Some embodiments of the voltage source can be configured to generate variable voltage pulse widths and/or various pulse shapes, such as square or sinusoidal pulse shapes.

FIG. 1E shows a plan view of another example spinal cord stimulator device 100 of the disclosure, and FIG. 1F shows a detailed plan view of part of the device 100, e.g., serpentine thin film electrode leads.

Embodiments of the device 100 depicted in FIG. 1E can have the same embodiments of implantation paddle 105 dimensions, polymer layers 120, 122, electrode stimulation pads and thin film electrode lead dimensions and compositions, thin film connection segment 107, encapsulant 110 and voltage source 180, as disclosed in the context of FIGS. 1A-1D. However, as illustrated in FIG. 1E, embodiments of electrode stimulation pads 112a, 113a can be circularly shaped (e.g., 50 micron diameter circles having an area of about 2000 microns). In other embodiments, however, the stimulation pads 112a, 113a of the device depicted in FIG. 1E having rectilinear-shaped pads could be used.

As illustrated in FIG. 1E, in some embodiments of the device 100, to facilitate having a narrower width paddle 105, the pair of pads 112a, 113a can be substantially aligned with each other and with a long axis 184 of the paddle 105.

As illustrated in FIG. 1E, to provide greater resistance to shear fracturing, for some embodiments of the device 100, the separate thin film electrode leads 116a, 117a that are separately connected to electrode stimulation pads 112a, 113a can include a serpentine profile, e.g., the profile in a plane parallel to the major surface 186 of the paddle 105.

For example, as illustrated in FIG. 1F, portions of the thin film electrode leads 116a, 117a can have a sinusoidal profile. In some embodiments, for example, the pitch 188 of the sinusoid can equal a value in a range from about 500 to 600 microns and the amplitude 190 of the sinusoid can equal a value in a range from about 250 to 300 microns. Embodiments of the film electrode leads 116a, 117a can have the same width 148 and edge-to-edge separation distance 152 as disclosed in the context of FIG. 1C.

Another embodiment of the disclosure is a method of manufacturing a spinal cord stimulator device. FIG. 2 presents a flow diagram of an example method 200 of manufacturing a spinal cord stimulator device such as any of the embodiments of the example devices 100 disclosed herein, e.g., such as discussed in the context of FIGS. 1A-1F.

With continuing reference to FIGS. 1A-1E, as illustrated in FIG. 2, the method 200 can include providing an implantation paddle 105 (step 210). As discussed in the context of FIGS. 1A-1E, the implantation paddle 105 can include at least one pair of electrode stimulation pads 112a, . . . , 113a, . . . each of the electrode stimulation pads connected to ends 115 of separate thin film electrode leads 116a, . . . 117a, . . . and the electrode stimulation pads and the thin film electrode leads sandwiched between softening polymer layers 120, 122.

In some embodiments, providing the implantation paddle 105 (step 210) can include manufacturing procedures such as described in the experiment section herein. One skilled in the pertinent art would understand how to adapt such procedures to provide any of the embodiments of the paddle 105 in accordance with step 210.

The method 200 can include connecting one end 126 of insulated wire leads 124a, . . . , 125a, . . . to contact pads 127a, . . . 128a, . . . of the opposite ends 129 of each one of the thin film electrode leads 116a, . . . 117a, . . . by forming separated coupling joints 130 (step 220).

In some embodiments, connecting the ends 126 of insulated wire leads 124a, . . . , 125a, . . . to the contact pads 127a, . . . 128a, . . . (step 220) includes removing the insulation from one end 126 of the wires, placing the end 126 into a solder paste located in the openings (e.g., openings 192, FIG. 1D) formed in the second softening polymer layer 122 and then subjecting the device to a solder reflow process to reflow the solder paste and thereby form solder joints 130 to bond the contact pads and wire leads together.

The method 200 can further include encompassing portions (e.g., lengths 172) of the thin film leads and portions (e.g., length 174) of the insulated wire leads 124a, . . . , 125a, . . . in the vicinity of the coupling joints 130 with an encapsulant 110 (step 230).

In some embodiments, encompassing (step 230) includes placing one or more droplets of a silicone epoxy polymer in the vicinity of the coupling joints 130 and allowing the silicone epoxy polymer to cure.

Another embodiment is a method of spinal cord stimulation. FIG. 3 presents a flow diagram of an example method of spinal cord stimulation, using any of the example spinal cord stimulator devices 100 disclosed herein, e.g., such as discussed in the context of FIGS. 1A-2.

With continuing reference to FIGS. 1A-2, the method 300 can comprise passing the implantation paddle 105 of the spinal cord stimulator device 100 between two vertebrae of a spinal cord (step 310).

For example, the paddle 105, as well as parts of the connection segment 107 and the encapsulant 110, can be passed between two vertebrae in the cervical spine, the thoracic spine or the lumbar spine, e.g., between two vertebrae at the C3, C4 interspace in the cervical spinal column in order to wrap the paddle around the cervical enlargement on the spinal cord between areas C5 through T1.

The method 300 can further comprise inserting the implantation paddle 105 into an epidural or a subdural space between the spinal cord and the vertebra (step 320). A long axis 184 of the implantation paddle 105 can be aligned with a long dimension of the spinal cord. After implantation, the two softening polymer layers 120, 122 spontaneously soften and wrap around part of a circumference of the spinal cord.

For example, in some embodiments, as part of step 320 the paddle 105 can be inserted adjacent to the spinal column above the dura mater, while in other embodiments, the paddle 105 can be inserted subdurally, to facilitate closer proximity of the stimulation electrode pads to spinal nerves. Inserting the paddle subdurally can include cutting a slit in the dura, and inserting the rigid paddle through the slit under the dura.

Aspects of step 320 are further illustrated in FIGS. 4A and 4B, which present perspective partial view sketches of an implantation paddle 105 of the spinal cord stimulator device 100 of the disclosure: (A) immediately after inserting the implantation paddle 105 into an epidural or a subdural space between the spinal cord 410 and the vertebra (vertebra not shown for clarity) and (B) after a period time following implantation, respectively.

As illustrated in FIG. 4A, immediately following implantation a long axis 184 of the implantation paddle 105 is aligned with a long dimension 420 of the spinal cord 410 (e.g., part of the length of the spinal from the foramen magnum to the upper part of the lumbar region) and the major surface 186 of the paddle 105 including layers 120, 122 is still in its original, e.g., planar shape. As illustrated in FIG. 4B, after a period time following implantation (e.g., about 5 hours for some embodiments) the long axis 184 of the implantation paddle 105 is still aligned with a long dimension 420 of the spinal cord 410 but due to softening of the softening polymer layers 120, 122 the major surface 186 of the paddle 105 has wrapped around part of a circumference 530 of the spinal cord 410. E.g., portions 440, 445 of the paddle 105 lateral to the long axis 184 have curled to hug and conform to the shape of the spinal cord 410.

The method 300 can further comprise connecting one end (e.g., opposite ends 182) of the insulated wire leads 124a, . . . 125a, . . . to a voltage source 180 (step 330).

For example the encapsulant 110 and portions of the insulated wire leads 124a, . . . 125a, . . . can reside in between the two vertebrae and the ends 182 of the wire leads 124a, . . . 125a, . . . can reside in an interstitial space of the body, e.g., between the skin and spinal cord, and be connected to an implanted voltage source 180, e.g., implantable pulse generator. For example, the ends 182 of the wire leads 124a, . . . 125a, . . . can exit the body to connect to an external voltage source e.g., a non-implantable pulse generator (step 340).

The method 300 can further comprise applying a voltage from the voltage source 180 across the ends (e.g., opposite ends 182) of the wire leads 124a, . . . 125a, . . . to generate an electric field (e.g., field line 154) between the pair of electrode pads 112a, . . . , 113a, . . . (step 350).

For example, as disclosed elsewhere herein, the voltage source 180 can be configured to apply a series of voltage pulses between the pair of electrode pads.

EXPERIMENTS

To further illustrate various features of the disclosure, various prototype spinal cord simulator devices were manufactured and tested for their ability to be chronically implanted along the spinal cord of rats and to provide reproducible stimulation thresholds or sub-thresholds, as disclosed below.

Manufacture of Implantation Paddles

The monomers of SMP6 were spun onto a sacrificial glass slide and then the monomers were photo cured to form SMP6 (e.g., layer 120, FIG. 1C). The SMP6 layer and the sacrificial glass slide were post cured in a vacuum oven for 12 hours at a temperature of 120° C. A layer of gold (e.g., a 300 nm thick layer) was formed by e-beam evaporation onto the layer of post cured SMP6. After the gold deposition, a positive photoresist was spun onto the gold layer. The photoresist was patterned with a photomask to outline thin film electrode leads (e.g., leads 116a, . . . 117a, . . . FIG. 1B), including contact pads (e.g., pads 127a, . . . 128a, . . . FIG. 1B) and bases for the electrode stimulation pads (e.g., pads 112a, . . . , 113a, . . . FIG. 1B). The positive photoresist was not crosslinked in regions where the thin film electrode leads are to be located through a positive chrome mask (e.g., a serpentine pattern in some embodiments). The chrome mask and the excess crosslinked photoresist were removed, and then the partially constructed paddle was submerged in an etchant (e.g., developer MF-319, Shipley MA) to remove portions of the gold layer that were not covered. The etchant was diluted 10:1 with distilled deionized water such that the paddle soaked in the solution for between 28 and 32 seconds. The paddle was then removed and placed in a flood exposure such that the remaining photoresist was broken down and washed away.

A 250 nm thick layer (e.g., layer 140 FIG. 1C) of titanium nitride was sputtered onto the partially constructed paddle using a RF magnetron sputtering system from a Ti target, with oxygen and nitrogen ratios in the sputtering chamber controlled to control the ratio of titanium oxy-nitride to titanium nitride, which affects the final charge injection capacity of the device.

A positive photoresist was spun onto the partially constructed paddle and patterned through another chrome mask to define target locations of the electrode stimulation pads. The positive resist was degraded through a mask similar in size and location as the target locations of the electrode stimulation pads. The areas of the device where the TiN layer was to be removed were exposed to a developer (e.g., MF-319, Shipley MA) for 55 seconds during which some of the photoresist was etched back, and, titanium nitride was removed in all areas except where the target electrode stimulation pads were to reside by using a TiN etcher. The remaining photoresist covering the TiN electrodes was removed by placing the partially constructed paddle under 365 nm UV light during a flood exposure and submerging it to a developer.

A second SMP6 layer (e.g., layer 122 FIG. 1C) was formed by spinning monomers of SMP6 onto the partially constructed paddle and then photocuring and post curing. A hard mask of SiNi was deposited on the second SMP layer and then patterned to form a mask with openings over the electrode stimulation pad and contact pad locations. The device was then exposed to a reaction ion etch to remove overlying portions of the second SMP6 layer to form opening in the second SMP6 layer (e.g., opening 192 FIG. 1D) and thereby expose the electrode stimulation pads and the contact pads.

Manufacture of Spinal Cord Stimulation Device

The contact pads (e.g., pads 127a, . . . 128a FIG. 1D) of the paddle (e.g., paddle 105, FIG. 1E) were connected to insulated wire leads (e.g., 124a, . . . 125a, FIG. 1D) by removing the insulation from one end (e.g., end 126 FIG. 1A) of the wires and placing the end 126 into a solder paste located in the openings (e.g., openings 192 formed in the second SMP6 layer 122, FIG. 1D). The insulated wire lead was composed of stainless steel and had a diameter of 114.3 microns (CAT. 790500, A-M Systems, LLC, Carlsborg, Wash.). The solder paste was a lead free indium silver solder paste (e.g., indium:silver equal to about 97:3, from Indium Corporation, Clinton, N.Y.).

The device was then subject to a solder reflow process to reflow the solder paste and thereby form solder joints (e.g., joints 130, FIG. 1E) to bond the contact pads and wire leads together.

A silicone epoxy polymer (LOCTITE® M-21HP, Henkel, Rocky Hill, Conn.) was then placed in the vicinity of the solder joints to form the encapsulant (e.g., encapsulant 110 FIG. 1E).

Prototype Spinal Cord Stimulator Devices and Spinal Cord Implantation

FIGS. 5A-5C present photographs of different prototype spinal cord stimulator devices of the disclosure manufactured as described above. The device shown in 5A was constructed to have an about 50 micron thick paddle (e.g., two 25 micron thick softening polymer layers), while the devices of FIGS. 5A and 5B were constructed to have an about 100 micron thick paddles (e.g., two 50 micron thick softening polymer layers).

The devices illustrated in FIGS. 5A and 5B were designed to have implantation paddles several times longer than the length target portion of the spinal cord to be stimulated in rat subjects. Thus, portions of these implantation paddles not implanted adjacent to the spinal cord, were extended between two vertebra and past the neck of the rat subjects such that ends of the thin film leads were coupled to connectors (e.g., pins 510 or leads 515, e.g., mounted to a head cap, not shown) which in turn were connected to a voltage source (not shown).

We discovered that prototype devices such as shown in FIG. 5A were subject to shearing damage, either in the region of the paddle that extended between the vertebra (e.g., region 520) and/or in the region of the paddle in the vicinity of the neck (e.g., region 525), e.g., due substantial movement in these regions. Prototype devices such as shown in FIG. 5B, with double the thickness of paddle, were more resistant to shearing but still, after a period of time (e.g., days), would also tend to shear in these same regions 520, 525.

To mitigate against such shearing damage, prototype devices such as shown in FIG. 5C were constructed to have a short paddle length which could be fully or near fully implanted in the epidural or subdural space and thus lay fully or near fully parallel to target portion of the spinal cord. The thin film electrode leads in the paddle were connected to the insulated wire leads as described elsewhere herein. While not limiting the disclosure by theoretical considerations, we believe that such wires are not as prone to shearing because they composed of a material, steel, resistant to shearing forces, and because the wires are relatively freer to rotate, bend and twist, e.g., during spinal cord or neck movement, than the devices shown in 5A and 5B with extended paddle lengths.

Spinal Cord Stimulator Device Implantation and Nerve Stimulation Testing

FIG. 6A shows a plan view photograph of an example spinal cord stimulator device of the disclosure during implantation under the C2 through C6 vertebra of a rat spinal cord and FIG. 6B presents a plan view photograph of the example spinal cord stimulator device depicted in FIG. 6A, prior to implantation.

FIGS. 7A and 7B present axial MRI views of implanted spinal cord stimulator devices of the disclosure that include implantation paddles 105 having softening polymer layers or parylene-C layers, respectively, three weeks after implantation adjacent to the spinal cords of rats.

As illustrated in FIG. 7A, the width (e.g., width 137 FIG. 1B) of the paddle 105, due to the softening of the softening polymer layers, curved to conform to the natural curvature of the spine, and hugged a portion of the curving circumference 430 of the spine. In contrast, as shown in FIG. 7B, the implanted paddle 105 having parylene-C layers, remained planar and did not conform the natural curvature of the spine. Rather, such paddles 105, having parylene-C layers, distorted a portion the spine's circumference so as to become flattened and more planar.

FIGS. 8A and 8B show post-mortem anterior posterior pictures of portions of rat spinal cord (e.g., spanning a length adjacent to T1 to C3 vertebra) one week post-implantation with dummy paddles (e.g., paddles without electrode stimulation pads or thin film electrode leads) having: (A) softening polymer layers or (B) parylene-C layers. As illustrated, there was more visible tissue damage to spinal cord implanted with the dummy paddles having parylene-C layers as compared to the spinal cord implanted with the dummy paddles having softening polymer layers.

Histopathology conducted on such spinal cord tissue post-implantation showed that GFAP (astrocyte) and ED-1 (macrophage) staining indicated no astrogliosis or macrophage reaction to implantation after 3 weeks with paddles having softening polymer layers.

Experiments were performed to test the function and electrical stability, both intraoperatively and postoperatively, in vivo in rats implanted with prototype devices similar to that depicted in FIG. 5C using paddles having softening polymer layers or parylene-C layers.

A laminectomy was performed at C3 and the implantation paddle was inserted into the epidural space to the C5-C6 level. The paddle was not anchored in the epidural space after insertion. Insulated wire leads (e.g., of the connection segment) were run up from the laminectomy through muscle and secured to the top of the rat's skull with dental cement. An A-M Systems Isolated Pulse Stimulator (A-M Systems, Carlsborg, Wash.) was used to stimulate the cervical spinal cord.

As illustrated in FIGS. 9-13B the results of these tests demonstrate that the disclosed spinal cord stimulator devices performs safely and reliably as expected in vivo over an extended period of time, and, devices with paddles having softening polymer layers were more sensitive then devices with paddles having parylene-C layers.

FIG. 9 presents an example electromyogram of the muscle response from a rat implanted with a spinal cord stimulator device of the disclosure when stimulated above a stimulation threshold in accordance with the disclosure.

FIG. 10 shows example the spinal cord stimulation thresholds ("spinal threshold") to evoke a muscle response measured via electromyography, measured in rats implanted with spinal cord stimulator devices that include implantation paddles having softening polymer layers ("softening electrode") or parylene-C layers ("parylene-C"), respectively. As illustrated rats implanted with paddles having softening polymer layers required substantial lower threshold than rats implanted with paddles having parylene-C layers.

FIG. 11 shows spinal cord stimulation thresholds, generated similar to that described in the context of FIGS. 9-10, over time for two rat subjects (S1, S2) implanted with spinal cord stimulator devices that include implantation paddles having softening polymer layers. As illustrated, spinal threshold remained substantially constant for several weeks post-implantation. This suggests no or minimal migration of the electrode stimulation pads from their originally implanted locations.

FIG. 12A show example changes in the electromyogram measured muscle response ("% change in EMG"), in rats implanted with spinal cord stimulator devices that include implantation paddles having softening polymer layers ("softening electrode") or parylene-C layers ("parylene-C"), respectively. FIG. 12B presents a sketch illustrating aspects of a method of stimulating the spinal cord of rats implanted with spinal cord stimulator devices after paired brain and spinal cord sub-threshold stimulation to evoke the EMG responses such as depicted in FIG. 12A.

As illustrated in FIG. 12B paired brain and spinal cord sub-threshold stimulation included sub-threshold stimulation of cortical regions of rat brain that map to forelimb function using conventional cortical electrodes, followed by an about 8 to 12 ms delay (e.g., 10 ms in some embodiments) and then subthreshold stimulation of nerves of the spinal cord using the implanted spinal cord stimulator device. As illustrated in FIG. 12A, much greater evoked muscle responses from such paired sub-threshold stimulation was obtained from rats implanted with paddles having softening polymer layers as compared to rates implanted with paddles having parylene-C layers.

FIG. 13A presents example changes in the electromyogram measured muscle response ("% change in EMG"), in rats implanted with spinal cord stimulator devices that include stimulating electrode portions having softening polymer layers ("softening electrode") or parylene-C layers ("paralene-C"), respectively, for different times after paired brain and spinal cord sub-threshold stimulation. FIG. 13B presents a sketch illustrating aspects of stimulating the spinal cord of rats implanted with spinal cord stimulator devices with different timing to evoke the EMG responses such as depicted in FIG. 13A.

Those skilled in the art to which this application relates will appreciate that other and further additions, deletions, substitutions and modifications may be made to the described embodiments.

What is claimed:

1. A spinal cord stimulator device, comprising:
an implantation paddle, the implantation paddle including:
softening polymer layers;
at least one pair of electrode stimulation pads, each of the electrode stimulation pads connected to ends of separate thin film electrode leads, wherein the electrode stimulation pads and the thin film electrode leads are sandwiched between the softening polymer layers;
a connection segment including:
insulated wire leads, and
coupling joints, wherein:
one end of each of the wire leads is connected to contact pads, at the coupling joints, to opposite ends of each one of the thin film leads, and
each of the coupling joints are separated from all others of the coupling joints; and
an encapsulant encompassing portions of the implantation paddle, including encompassing portions of the softening polymer layers surrounding the contact pads, the coupling joints and portions of the connection segment including portions of the wire leads next to the coupling joints, wherein the softening polymer layers are composed of polymers formed from combinations of monomers functionalized with thiol-enes, thiol-ene or acrylates, and having a glassy modulus in a range from about 1 to 3 GPa at room temperature in an air environment and a rubbery plateau in a range from about 100 MPa to 0.03 MPa at about 37° C. in an aqueous environment.

2. The device of claim 1, wherein the softening polymer layers are composed of polymers formed from a stoichiometric combination of the monomers Tris[2-(3-mercaptopropionyloxy)ethyl] isocyanurate (TMICN) and 1,3,5-triallyl-1,2,5-triazine-2,4,6 (1H,3H,5H)-trione (TATATO) combined with 31 mol % Tricyclo[5.2.1.02,6]decanedimethanol diacrylate (TCMDA).

3. The device of claim 1, wherein the softening polymer layers have an elastic modulus equal to about 1.8 GPa at 21° C. in an air environment and an elastic modulus equal to about 50 MPa at 37° C. in an aqueous environment.

4. The device of claim 1, wherein each of the softening polymer layers have a thickness in a range from about 20 to 100 microns.

5. The device of claim 1, wherein each of the softening polymer layers have ratio of width to long axis length in a range from about 1:6 to 1:8.

6. The device of claim 1, wherein the implantation paddle further includes a lead segment that includes the softening polymer layers and is free of the electrode stimulation pads and the thin film traces.

7. The device of claim 1, wherein the coupling joints include a lead free indium silver solder.

8. The device of claim 1, wherein the encapsulant is composed of a silicone epoxy polymer.

9. The device of claim 1, wherein each of the thin film electrode leads have a serpentine profile in a plane parallel to a major surface of the paddle.

10. The device of claim 1, wherein each of the thin film electrode leads are composed of a layer gold located on one of the softening polymer layers, the layer of gold having a thickness in a range from about 100 nm to 5000 nm.

11. The device of claim 1, wherein each of the thin film electrode leads are composed of copper, nickel, aluminum, platinum, PEDOT, carbon nanotubes, graphene, ultrananocrystalline diamond, chromium, or alloys palladium, nickel and gold.

12. The device of claim 1, wherein each of the electrode stimulation pads have an area perimeter in a range from about 2 $mm^2$ to 6 $mm^2$.

13. The device of claim 1, wherein an edge-to-edge distance between the pair of electrode stimulation pads is in a range from about 1 to 10 mm.

14. A method of manufacturing a spinal cord stimulator device, comprising:
providing an implantation paddle, the implantation paddle including:
softening polymer layers;
at least one pair of electrode stimulation pads, each of the electrode stimulation pads connected to ends of separate thin film electrode leads, wherein the electrode stimulation pads and the thin film electrode leads are sandwiched between the softening polymer layers;
connecting one end of insulated wire leads to contact pads, at coupling joints, to opposite ends of each one of the thin film electrode leads wherein each of the coupling joints are separated from all others of the coupling joints; and
encompassing portions of the thin film electrode leads and portions of the insulated wire leads in the vicinity of the coupling joints with an encapsulant, wherein the softening polymer layers are composed of polymers formed from combinations of monomers functionalized with thiol-enes, thiol-ene or acrylates, and having a glassy modulus in a range from about 1 to 3 GPa at room temperature in an air environment and a rubbery plateau in a range from about 100 MPa to 0.03 MPa at about 37° C. in an aqueous environment.

15. The method of claim 14, wherein forming the coupling joints includes:
removing insulation from one end of the wire leads,
placing the one end into a solder paste in an opening formed in the second softening polymer layer, and
subjecting the device to a solder reflow process to reflow the solder paste and thereby form the solder joint.

16. The method of claim 14, wherein encompassing includes placing one or more droplets of a silicone epoxy polymer in the vicinity of the coupling joints and curing the silicone epoxy polymer.

17. A method of spinal cord stimulation, comprising:
passing an implantation paddle of a spinal cord stimulator device between two vertebrae of a spinal cord, wherein:
the implantation paddle includes softening polymer layers and at least one pair of electrode stimulation pads, each of the electrode stimulation pads connected to ends of separate thin film electrode leads, wherein the electrode stimulation pads and the thin film electrode leads are sandwiched between the softening polymer layers, and
the spinal cord stimulator device further includes:
a connection segment including insulated wire leads and coupling joints, wherein one end of each of the wire leads is electrically connected to contact pads on opposite ends of each one of the thin film leads at the coupling joints, wherein each of the coupling joints are separated from all others of the coupling joints; and
an encapsulant encompassing portions of the implantation paddle, including encompassing portions of the softening polymer layers surrounding the contact pads, the coupling joints and portions of the connection segment including portions of the wire leads next to the coupling joints, wherein the softening polymer layers are composed of polymers formed from combinations of monomers functionalized with thiol-enes, thiol-ene or acrylates, and having a glassy modulus in a range from about 1 to 3 GPa at room temperature in an air environment and a rubbery plateau in a range from about 100 MPa to 0.03 MPa at about 37° C. in an aqueous environment; and inserting the implantation paddle into an epidural or a subdural space between the spinal cord and the vertebra, wherein a long axis of the implanted implantation paddle is aligned with a long dimension of the spinal cord, and after implantation, the two softening polymer layers soften and wrap around part of a circumference of the spinal cord.

18. The method of claim 17, further including connecting ends of the wire leads to a voltage source.

19. The method of claim 17, further including applying a voltage from the voltage source across the ends of the wire leads to generate an electric field between the pair of electrode pads.

* * * * *

UNITED STATES PATENT AND TRADEMARK OFFICE
CERTIFICATE OF CORRECTION

PATENT NO. : 10,786,671 B2
APPLICATION NO. : 16/344100
DATED : September 29, 2020
INVENTOR(S) : Walter E. Voit, Aldo Garcia-Sandoval and Jason Carmel Page 1 of 1

It is certified that error appears in the above-identified patent and that said Letters Patent is hereby corrected as shown below:

In the Specification

In Column 7, Line 54, delete "about 700 to 3000 microns" and insert --about 700 to 3000 microns $_2$--

In Column 9, Line 5, delete "about 2000 microns)" and insert --about2000 microns$_{2)}$--

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*